(12) United States Patent
Novak et al.

(10) Patent No.: US 11,919,100 B2
(45) Date of Patent: Mar. 5, 2024

(54) ACCESSORIES FOR OSCILLATING POWER TOOLS

(71) Applicant: BLACK & DECKER INC., New Britain, CT (US)

(72) Inventors: Joseph T. Novak, East Longmeadow, MA (US); Kevin Howe, Ludlow, MA (US); Kenneth Hall, East Longmeadow, MA (US)

(73) Assignee: THE BLACK & DECKER CORPORATION, Towson, MD (US)

( * ) Notice: Subject to any disclaimer, the term of this patent is extended or adjusted under 35 U.S.C. 154(b) by 265 days.

(21) Appl. No.: 17/179,831

(22) Filed: Feb. 19, 2021

(65) Prior Publication Data

US 2021/0276111 A1 Sep. 9, 2021

Related U.S. Application Data

(60) Provisional application No. 62/981,223, filed on Feb. 25, 2020.

(51) Int. Cl.
*B23D 61/00* (2006.01)
*B27B 19/00* (2006.01)

(52) U.S. Cl.
CPC .......... *B23D 61/006* (2013.01); *B27B 19/006* (2013.01)

(58) Field of Classification Search
CPC ...... B23D 61/006; B23D 51/00; B23D 49/11; B23D 61/123; B23D 61/126; B25F 3/00; B27B 19/006; A51B 17/142; A61B 17/144
USPC ...... 30/355, 392, 144, 166.3, 342, 346, 351, 30/353, 356, 502, 505, 122, 393, 394, 30/277.4; 83/835, 837, 838, 846, 847, 83/848, 849, 850, 851, 852, 853, 854, 83/750; D8/20, 70, 96, 98, 100, 101; D24/146, 147
See application file for complete search history.

(56) References Cited

U.S. PATENT DOCUMENTS 3,977,289 A 8/1976 Tuke
4,617,930 A 10/1986 Saunders
(Continued)

FOREIGN PATENT DOCUMENTS

DE 4425456 A1 3/1996
DE 202004007929 U1 7/2004
(Continued)

OTHER PUBLICATIONS

European Search Report for EP Application No. 21159038.5 dated Jun. 25, 2021, 8 pages.

*Primary Examiner* — Ghassem Alie
(74) *Attorney, Agent, or Firm* — Scott B. Markow

(57) ABSTRACT

An accessory for an oscillating power tool includes an attachment portion configured to be coupled to an oscillating power tool and a working portion extending generally along a longitudinal axis. The working portion has a rear end portion coupled to the attachment portion, a front cutting edge opposite the rear end portion, a first side edge extending from the front cutting edge to the rear end portion, and a second side edge opposite the first side edge and extending from the front cutting edge to the rear end portion. The working portion includes an at least partially curved surface that contains the longitudinal axis. At least a portion of the first side edge includes a first side cutting edge portion.

20 Claims, 27 Drawing Sheets

(56) References Cited

U.S. PATENT DOCUMENTS

| | | | |
|---|---|---|---|
| 5,964,039 A | 10/1999 | Mizoguchi et al. | |
| 7,833,241 B2 * | 11/2010 | Gant | A61B 17/1637 30/392 |
| D693,193 S | 11/2013 | Bozic | |
| D741,135 S | 10/2015 | Yang et al. | |
| D741,136 S | 10/2015 | Yang et al. | |
| 9,527,146 B2 | 12/2016 | Stoddart et al. | |
| D814,900 S | 4/2018 | Kaye et al. | |
| D817,127 S | 5/2018 | Gopi | |
| D817,128 S | 5/2018 | Gopi | |
| D832,666 S | 11/2018 | Kaye et al. | |
| 10,307,917 B2 | 6/2019 | Marks | |
| 10,427,229 B2 | 10/2019 | Karlen | |
| 10,792,740 B2 | 10/2020 | Karlen | |
| 10,799,968 B2 | 10/2020 | Bozic | |
| 2002/0042998 A1 * | 4/2002 | Napoli | B23D 61/123 30/277.4 |
| 2002/0104421 A1 | 8/2002 | Wurst | |
| 2010/0218655 A1 * | 9/2010 | Gillette | B23D 61/123 83/56 |
| 2010/0288099 A1 | 11/2010 | Steiger | |
| 2014/0015207 A1 | 1/2014 | Kaye et al. | |

FOREIGN PATENT DOCUMENTS

| | | |
|---|---|---|
| DE | 102011103880 A1 | 11/2012 |
| DE | 102012201667 A1 | 8/2013 |
| FR | 986764 A | 8/1951 |
| WO | 8606609 A1 | 11/1986 |
| WO | 2013113523 A1 | 8/2013 |
| WO | 2015169143 A1 | 11/2015 |
| WO | 2016132320 A1 | 8/2016 |

\* cited by examiner

ACCESSORIES FOR OSCILLATING POWER TOOLS

RELATED APPLICATION

This application claims priority, under 35 U.S.C. § 119(e), to U.S. Provisional Patent Application No. 62/981,223, filed Feb. 25, 2020, titled "Accessories For Oscillating Power Tools," which is incorporated by reference.

TECHNICAL FIELD

This application relates to accessories (such as cutting tools and saw blades) for oscillating power tools.

BACKGROUND

Oscillating power tools generally have a motor, an output shaft, and a transmission that connects the motor to the output shaft and converts rotary motion of the motor to oscillating motion of the output shaft. The output shaft is coupled to an accessory attachment mechanism that is used to removably attach various types of accessories, such as cutting tools, saw blades, and sanding tools, to the output shaft. It is desirable to have oscillating accessories for performing variety of tasks.

SUMMARY

In an aspect, an accessory for an oscillating power tool includes an attachment portion configured to be coupled to an oscillating power tool and a working portion extending generally along a longitudinal axis. The working portion has a rear end portion coupled to the attachment portion, a front cutting edge opposite the rear end portion, a first side edge extending from the front cutting edge to the rear end portion, and a second side edge opposite the first side edge and extending from the front cutting edge to the rear end portion. The working portion an at least partially curved surface that contains the longitudinal axis, at least a portion of the first side edge comprising a first side cutting edge portion.

Implementations of this aspect may include one or more of the following features. The second side edge may have a second side cutting edge portion. The first side cutting edge portion and/or the second side cutting edge portion may be adjacent the front cutting edge. The first side edge and the second side edge may be parallel. The attachment portion may include a planar portion that lies generally in a first plane. The at least partially curved surface may be tangent to a second plane that is generally parallel to the first plane, perpendicular to the first plane, or at transverse (e.g., at an acute angle) to the first plane. The at least partially curved surface may have a bottom concave face that faces down relative to the attachment portion. The at least partially curved surface may have a top concave face that face upward relative to the attachment portion. The front cutting edge may be straight when viewed from a top of the working portion. The front cutting edge may be curved along a concave curve facing toward the attachment portion when viewed from a top of the working portion. The working portion may have a first width that is substantially the same as a second width of the attachment portion. The working portion may have a first width that is less than a second width of the attachment portion.

The at least partially curved surface may have a curvature with a radius. The radius may be between approximately 2 inches and approximately 8 inches. The at least partially curved surface may define a cord extending from the first side edge to a second side edge. The cord may have a cord length between approximately 0.70 inches and approximately 2 inches. The at least partially curved surface further defines a sagitta extending from the longitudinal axis to the cord perpendicular to the cord. The sagitta may have a length between approximately 0.015 inches and approximately 0.127 inches.

The first cutting edge may have a first plurality teeth and the first side cutting edge portion has a second plurality of teeth. The first plurality of teeth may be configured differently than the second plurality of teeth. The first plurality of teeth may have a first tooth pitch and the second plurality of teeth may have a second tooth pitch that is different than the first tooth pitch. The first tooth pitch may be greater than the second tooth pitch. The first tooth pitch may be less than the second tooth pitch. The working portion may be symmetrical about the longitudinal axis. The working portion may be configured to cut a curved or circular opening in a workpiece. The at least partially curved surface may have a curvature with a radius that is less than or equal to a radius of a curved or circular opening to be cut in a workpiece.

In another aspect, an accessory for an oscillating power tool includes an attachment portion configured to be coupled to an oscillating power tool. The attachment portion includes a planar portion lying in a first plane. A working portion extends generally along a longitudinal axis and includes a rear end portion coupled to the attachment portion, a curved front cutting edge opposite the rear end portion, a first side edge extending from the front cutting edge to the rear end portion, and a second side edge opposite the first side edge and extending from the front cutting edge to the rear end portion. The working portion includes an at least partially curved surface that contains the longitudinal axis, where the longitudinal axis is transverse to the first plane.

Implementations of this aspect may include one or more of the following features. The at least partially curved surface may have a bottom concave face that faces toward the attachment portion. The longitudinal axis may be transverse (e.g., perpendicular or at an acute angle) to an oscillating axis about which the attachment portion oscillates when the attachment portion is coupled to the oscillating power tool. The longitudinal axis may be parallel to an oscillating axis about which the attachment portion oscillates when the attachment portion is coupled to the oscillating power tool. The curved cutting edge may have a radius of curvature that is centered at the oscillating axis or that is centered at a point that is rearward or forward of the oscillating axis. The radius may be between approximately 2 inches and approximately 8 inches. The at least partially curved surface may define a cord extending from the first side edge to a second side edge. The cord may have a cord length between approximately 0.70 inches and approximately 2 inches. The at least partially curved surface further defines a sagitta extending from the longitudinal axis to the cord perpendicular to the cord. The sagitta may have a length between approximately 0.015 inches and approximately 0.127 inches.

The first cutting edge may have a first plurality teeth and the first side cutting edge portion has a second plurality of teeth. The first plurality of teeth may be configured differently than the second plurality of teeth. The first plurality of teeth may have a first tooth pitch and the second plurality of teeth may have a second tooth pitch that is different than the first tooth pitch. The first tooth pitch may be greater than the second tooth pitch. The first tooth pitch may be less than the second tooth pitch. The working portion may be symmetrical about the longitudinal axis. The working portion may be configured to cut a curved or circular opening in a workpiece. The at least partially curved surface may have a curvature with a radius that is less than or equal to a radius of a curved or circular opening to be cut in a workpiece.

A position of the working portion relative to the intermediate portion may be user adjustable between a rear position and a forward position, the rear position being closer to the attachment portion than the forward position. An intermediate portion may be coupled between the attachment portion and a rear planar portion of the working portion. At least one of the intermediate portion and the rear planar portion may define a slot therethrough to facilitate adjustment of the working portion position between the rear position and the forward position. A fastener may be receivable in the slot and configured to retain the working portion in a plurality of positions between the rear position and the forward position. The intermediate portion may be defined the slot, the rear planar portion may define an opening, and the fastener may be receivable through the slot and the opening. The fastener may be a threaded bolt and may be secured in a desired position in the slot by a threaded nut. The fastener may have a non-circular cross section to inhibit rotation of the working portion relative to the intermediate portion.

In another aspect, an accessory for an oscillating power tool includes an attachment portion including a planar portion that lies in a first plane. The attachment portion is configured to be coupled to an oscillating power tool. A working portion includes a rear end portion and a curved portion extending from the rear end portion along a longitudinal axis that is transverse to the first plane. The curved portion includes a curved front cutting edge opposite the rear planar portion, a first side edge extending from the front cutting edge toward the rear planar portion, and a second cutting edge opposite the first side cutting edge and extending from the front cutting edge toward the rear planar portion. The working portion is configured to cut a curved or circular opening in a workpiece. A position of the working portion relative to the attachment portion is user adjustable between a rear position and a forward position, the rear position being closer to the attachment portion than the forward position.

Implementations of this aspect may include one more of the following features. An intermediate portion may be coupled between the attachment portion and the working portion. At least one of the intermediate portion, the working portion, and the attachment portion defines a slot therethrough to facilitate the user adjustment of the position of the working portion between the rear position and the forward position. A fastener may be receivable in the slot and configured to retain the working portion in a plurality of positions between the rear position and the forward position. The rear end portion of the working portion may include a rear planar portion lying in a second plane parallel to the first plane. At least one of the intermediate portion and the rear planar portion may define a slot therethrough to facilitate adjustment of the working portion position between the rear position and the forward position. A fastener may be receivable in the slot and configured to retain the working portion in a plurality of positions between the rear position and the forward position. The intermediate portion may be defined the slot, the rear planar portion may define an opening, and the fastener may be receivable through the slot and the opening. The fastener may be a threaded bolt and may be secured in a desired position in the slot by a threaded nut. The fastener may have a non-circular cross section to inhibit rotation of the working portion relative to the intermediate portion.

The at least partially curved surface may have a bottom concave face that faces toward the attachment portion. The longitudinal axis may be transverse (e.g., perpendicular or at an acute angle) to an oscillating axis about which the attachment portion oscillates when the attachment portion is coupled to the oscillating power tool. The longitudinal axis may be parallel to an oscillating axis about which the attachment portion oscillates when the attachment portion is coupled to the oscillating power tool. The curved cutting edge may have a radius of curvature that is centered at the oscillating axis or that is centered at a point that is rearward or forward of the oscillating axis. The radius may be between approximately 2 inches and approximately 8 inches. The at least partially curved surface may define a cord extending from the first side edge to a second side edge. The cord may have a cord length between approximately 0.70 inches and approximately 2 inches. The at least partially curved surface further defines a sagitta extending from the longitudinal axis to the cord perpendicular to the cord. The sagitta may have a length between approximately 0.015 inches and approximately 0.127 inches.

The first cutting edge may have a first plurality teeth and the first side cutting edge portion has a second plurality of teeth. The first plurality of teeth may be configured differently than the second plurality of teeth. The first plurality of teeth may have a first tooth pitch and the second plurality of teeth may have a second tooth pitch that is different than the first tooth pitch. The first tooth pitch may be greater than the second tooth pitch. The first tooth pitch may be less than the second tooth pitch. The working portion may be symmetrical about the longitudinal axis. The working portion may be configured to cut a curved or circular opening in a workpiece. The at least partially curved surface may have a curvature with a radius that is less than or equal to a radius of a curved or circular opening to be cut in a workpiece.

Advantages may include one or more of the following. The oscillating accessories may be used for cutting a wide range of curved or circular holes using the same blade. The oscillating accessories may be used for cutting a variety of materials, such as drywall, plywood, wood, and metal. The curvature of the accessories act as a rudder and allow a user to easily follow a scribed circle allowing for easy hole creation. When cutting in drywall, this avoids rips and tears in the paper, enables a user to use less force, and results in more consistent hole shapes. These and other advantages and features will be apparent from the description, the drawings, and the claims.

DETAILED DESCRIPTION

Figure 1A:
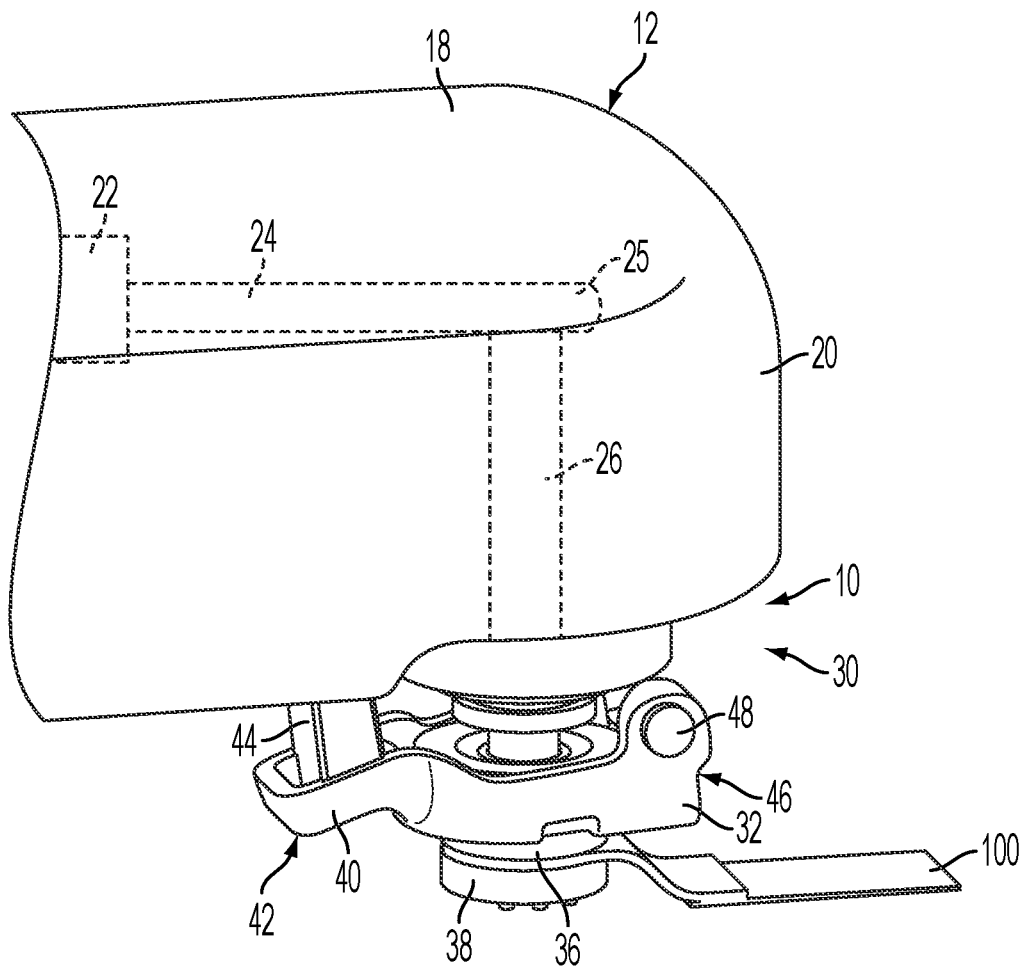
FIG. 1A is a perspective view an oscillating power tool having an implementation of an accessory attachment mechanism.
Figure 1B:
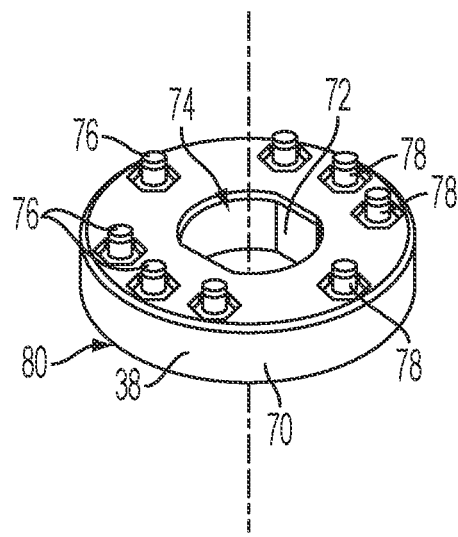
FIG. 1B a perspective view of a clamping plate of the attachment mechanism of FIG. 1A.

Referring to FIGS. 1A and 1B, in an implementation, an oscillating power tool 12 usable with the accessories described in this application is similar to oscillating power tools sold under the brand names DEWALT® and Porter-Cable® and is described further in U.S. Pat. No. 8,925,931, which is hereby incorporated by reference. The power tool 12 includes a tool body 18 including a housing 20 that contains a motor 22 to drive an output member 24. An output spindle 26 is coupled to the motor 22 via a transmission 25 that converts rotary motion of the motor 22 to oscillating motion of the spindle 26. The output of the spindle 26 is coupled to an accessory attachment mechanism 10 via an output shaft 102. The accessory attachment mechanism 10 does not require the use of a separate tool to couple an accessory or blade (such as the accessory 100 shown in FIGS. 2A-2B, as described below) to the oscillating power tool (also known as a "tool-free" attachment mechanism). An exemplary tool-free attachment mechanism 10 includes a clamp assembly 30 having a first clamp member 36 fixedly coupled to the output spindle, a second clamp member 38 facing the first clamp member 36, and a lever 32 coupled to the second clamp member 38. The lever 32 includes a lever arm 40 with a user engagement portion 42 and a block 44. The lever 32 further includes a pivot portion 46 having a pivot axle 48. The second clamp member 38 includes a second clamp body 70 generally in the form of a ring having a central opening 72. The second clamp body 70 has a second clamping surface 74 having a plurality of mounting features 76 formed thereon. In the example shown, the plurality of mounting features 76 are in the form of male projections 78. In the particular example shown, the eight male projections 78 each have a circular cross section and a tapered shape or form. In another related implementation, the male projections may have an oblong, oval, or rectangular cross-section and may also be tapered. In other implementations, the accessory 100 described below may be configured for use with or adapted for use with other oscillating power tools and accessory mounting mechanisms for oscillating power tools, such as those disclosed in U.S. patent application Ser. Nos. 16/511,043; 15/893,610; 15/253,559; 15/065,024; 14/909,233; 14/909,247; and Ser. No. 12/798,997; and U.S. Pat. Nos. 10,350,721; 10,137,592; 10,040,215; 9,670,998; 9,272,435; 9,346,183; 8,585,469; 8,182,316, each of which is incorporated by reference.

Figure 2:
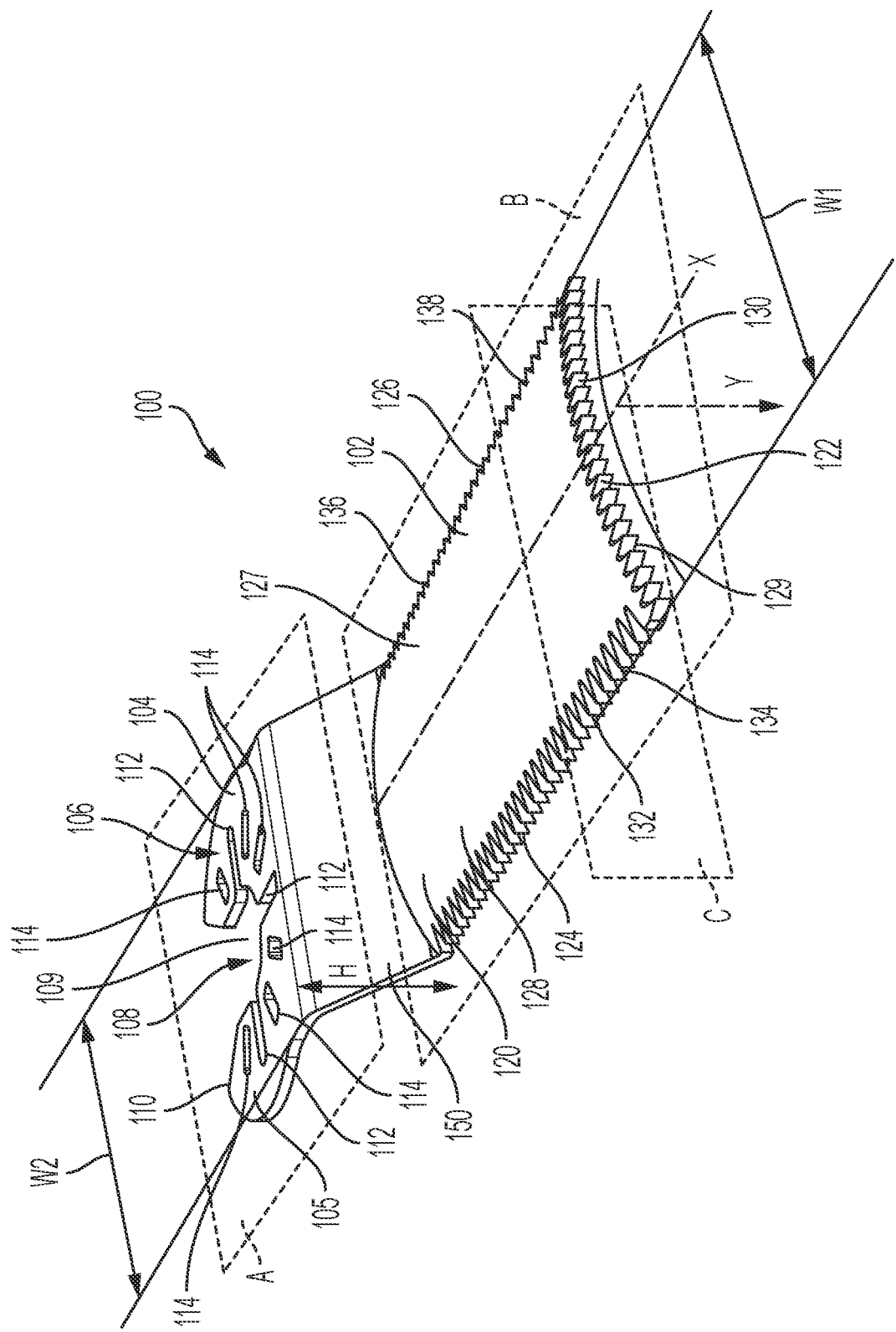
FIG. 2 is a perspective view of a first implementation of an oscillating accessory configured to be coupled to an attachment mechanism of an oscillating power tool, such as the power tool in FIGS. 1A-1B.
Figure 3:
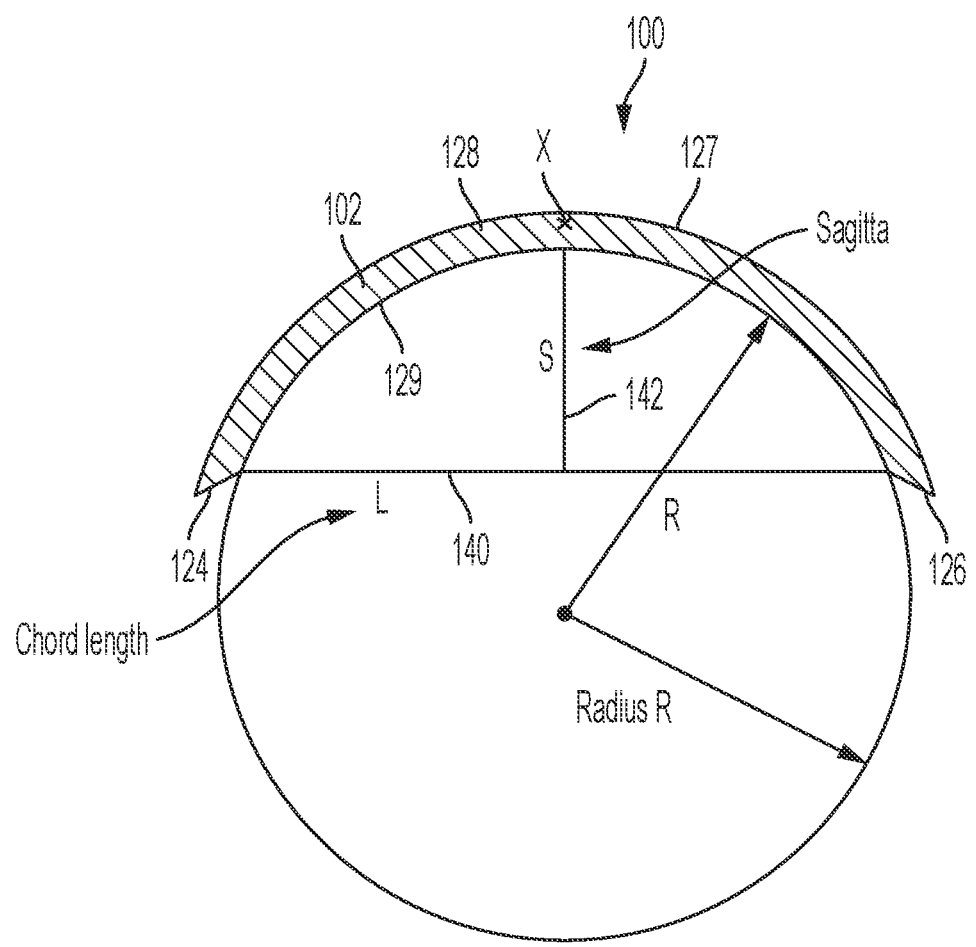
FIG. 3 is a cross-sectional view of a working portion of the accessory of FIG. 2, taken along a plane C.
Figure 4:
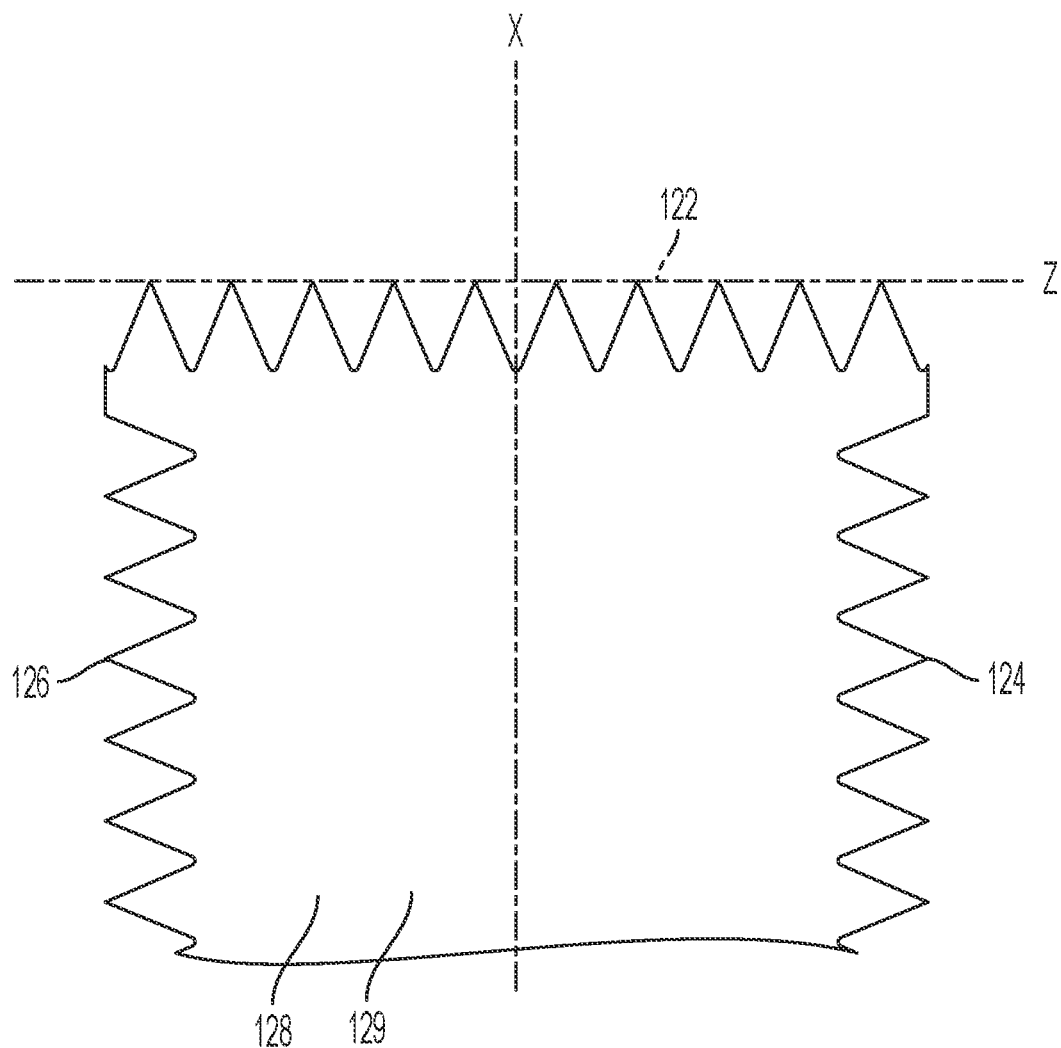
FIG. 4 is a top close-up view of the front cutting edge of the accessory of FIG. 3.

Referring also to FIGS. 2-4, an implementation of an oscillating accessory 100 includes a working portion 102 and an attachment portion 104. In one implementation, the attachment portion 104 includes a generally planar portion 105 lying generally in a first plane A. Defined in the generally planar portion 105 are a plurality of recesses or openings 106 configured to couple the accessory 100 to an attachment mechanism of an oscillating power tool, such as the attachment mechanism 10 of the oscillating power tool 12 described above or the other attachment mechanisms for oscillating power tools incorporated by reference and listed above. The openings 106 may include a generally U-shaped opening 108 extending from a rear end portion 110 of the accessory 100 and terminating in a central portion 109. A first set of three radial arm openings 112 are in communication with and extend radially outward from the central portion 108 at approximately 90°, approximately 180°, and approximately 270°, respectively, relative to the U-shaped opening 108. A second set of six radial openings 114 are spaced radially outward from and not in communication with the central portion 109, and are positioned at approximately 60°, approximately 120°, approximately 150°, approximately 210°, approximately 240°, and approximately 300° relative to the U-shaped opening 108. This configuration enable the attachment portion to be coupled to a wide variety of brands of power tools. In other implementations, the attachment portion may have a configuration similar to those shown, e.g., in U.S. Pat. Nos. 10,245,716 and 10,265,778, which are incorporated by reference. In certain implementations, the attachment portion may be universal or nearly universal and/or may be coupleable to two or more the oscillating power tools described and incorporated by reference above.

The working portion 102 is coupled to the attachment portion 104 and extends generally along a longitudinal axis X. The working portion 102 has a rear end portion 120 coupled to the attachment portion, a front cutting edge 122 opposite the rear end portion, a first side edge 124 extending from the front cutting edge toward the rear end portion 120, and a second side edge 126 opposite the first side edge 124 and extending from the front cutting edge 122 toward the rear end portion 120. The working portion 102 comprises an at least partially curved surface 128 that contains the longitudinal axis X and the extends from the first side edge 124 to the second side edge 126. At the longitudinal axis X, the at least partially curved surface 128 is tangent to a second plane B that is generally parallel to the first plane A and that contains the longitudinal axis X. The at least partially curved surface 128 has a generally convex upper face 127 and a generally concave lower face 129 that faces in a downward direction Y relative to the attachment portion 104.

The front cutting edge 122 may include a first plurality of cutting teeth 130. At least a portion of the first side edge 124 comprises a first cutting edge portion 132 with a second plurality of cutting teeth 134. At least a portion of the second side edge 126 comprises a second cutting edge portion 136 with a third plurality of cutting teeth 138. In the illustrated embodiment, the cutting teeth 130, 134, 138 extend along an entirety of the front cutting edge 122, the first side edge 124, and the second side edge 126, respectively. However, it should be understood that the cutting teeth each may extend along only a portion of their respective front cutting edge 122, first side edge 124, and second side edge 126. Also, in another embodiment, only one of the first side edge 124 and the second side edge 126 has a cutting edge portion, while the other has no cutting edge portion. In the illustrated embodiment, the first side cutting edge portion 132 and the second side cutting edge portion 136 are adjacent the front cutting edge 122. However, it should be understood that the first side cutting edge portion 132 and the second side cutting edge portion 136 may be spaced from the front cutting edge 122 by non-cutting portions of the first side edge 124 and the second side edge 126, respectively. In the illustrated embodiment, the first side edge 124 and the second side edge 126 are generally parallel. However, it should be understood that they may converge toward or diverge away from one another as they extend from the rear end portion 120 toward the front cutting edge 130 and/or may have a non-linear shape. In the illustrated embodiment, the working portion 102 is generally symmetrical about the longitudinal axis X. However, it should be understood that the working portion 128 may be assymetrical. As shown in FIG. 4, in the illustrated embodiment, the front cutting edge 122 is a single straight edge with the teeth aligned along a line Z when viewed from a top of the working portion 128. However, it should be understood that the front cutting edge 122 may have multiple straight sections, with some at an angle to the axis X and/or may be fully or partially curved.

In certain implementations, the first plurality of teeth 130, the second plurality of teeth 134, and/or the third plurality of teeth 138 may be configured to be the same or different from one another. For example, the first plurality of teeth 130 may have a different pitch (teeth per inch or tpi), tooth height, tooth width, tooth thickness, set pattern, gullet depth, rake angle, relief angle, top bevel angle, and/or side bevel angle than the second and third plurality of teeth 134, 138. In one exemplary implementation, the first plurality of teeth 130 has a first tooth pitch and the second and third plurality of teeth 134, 138 each have a second tooth pitch that is different than the first tooth pitch. For example, the first tooth pitch (e.g., approximately 10 tpi to approximately 32 tpi) may be greater than the second tooth pitch (e.g., approximately 8 tpi to approximately 20 tpi). In other examples, the first tooth pitch (e.g., approximately 8 tpi to approximately 20 tpi) may be greater than the second tooth pitch (e.g., approximately 10 tpi to approximately 32 tpi). In still other examples, one of the first and second tooth pitches may be variable, while the other may be constant.

When viewed in the cross-sectional view of FIG. 3, the at least partially curved surface 128 has a curvature with a radius R. The radius R may be between approximately 1 inches and approximately 8 inches (e.g., approximately 3 inches). In the illustrated embodiment, the curvature and radius are constant. However, it should be understood that the at least partially curved surface 128 may have a variable curvature or radius and may have a portion that is not curved. The at least partially curved surface 128 also defines a cord 140 extending from the first side edge 124 to the second side edge 126. The cord 140 may have a cord length L between approximately 0.5 inches and approximately 2 inches (e.g., approximately 1.5 inches). The at least partially curved surface 128 may further defines a sagitta 142 extending from the longitudinal axis X to the cord 140 perpendicular to the cord 140. The sagitta 142 may have a length S between approximately 0.004 inches and approximately 0.172 inches (e.g., approximately 0.128 inches). The working portion 102 has a first width W1 that is approximately the same as a second width W2 of the attachment portion W1 (e.g., approximately 0.5 inches to approximately 2.0 inches, such as approximately 0.7 inches).

The working portion 102 may be connected to the attachment portion 104 by an intermediate portion 150, such that the first plane A and the second plane B are offset from one another by a height H (e.g., approximately 0.3 inches to approximately 0.6 inches). The intermediate portion 150 may disposed at a right angle or an acute angle (e.g., approximately 15° to approximately 89°) to the attachment portion 104. This offset may make it easier for the working portion 102 to plunged deeper into a workpiece without interference from the clamp assembly 30 on the oscillating power tool 12. In other implementations, the first plane A and the second plane B may be substantially co-planar (or have portions that are substantially co-planar) or may substantially lie (or have portions that substantially lie) in planes that are at an angle to one another. It will be understood to one of ordinary skill in the art that the attachment portion 104 may not be planar but instead may have portions that substantially lie in or along a plane.

The working portion 102 is configured to cut a curved or circular opening in a workpiece such as drywall. The at least partially curved surface may have a curvature with a radius that is less than or equal to a radius of a curved or circular opening to be cut in the workpiece. The curvature of the accessories act as a rudder and allow a user to easily follow a scribed circle allowing for easy hole creation. When cutting in drywall, this avoids rips and tears in the paper, enables a user to use less force, and results in more consistent hole shapes.

Figure 5:
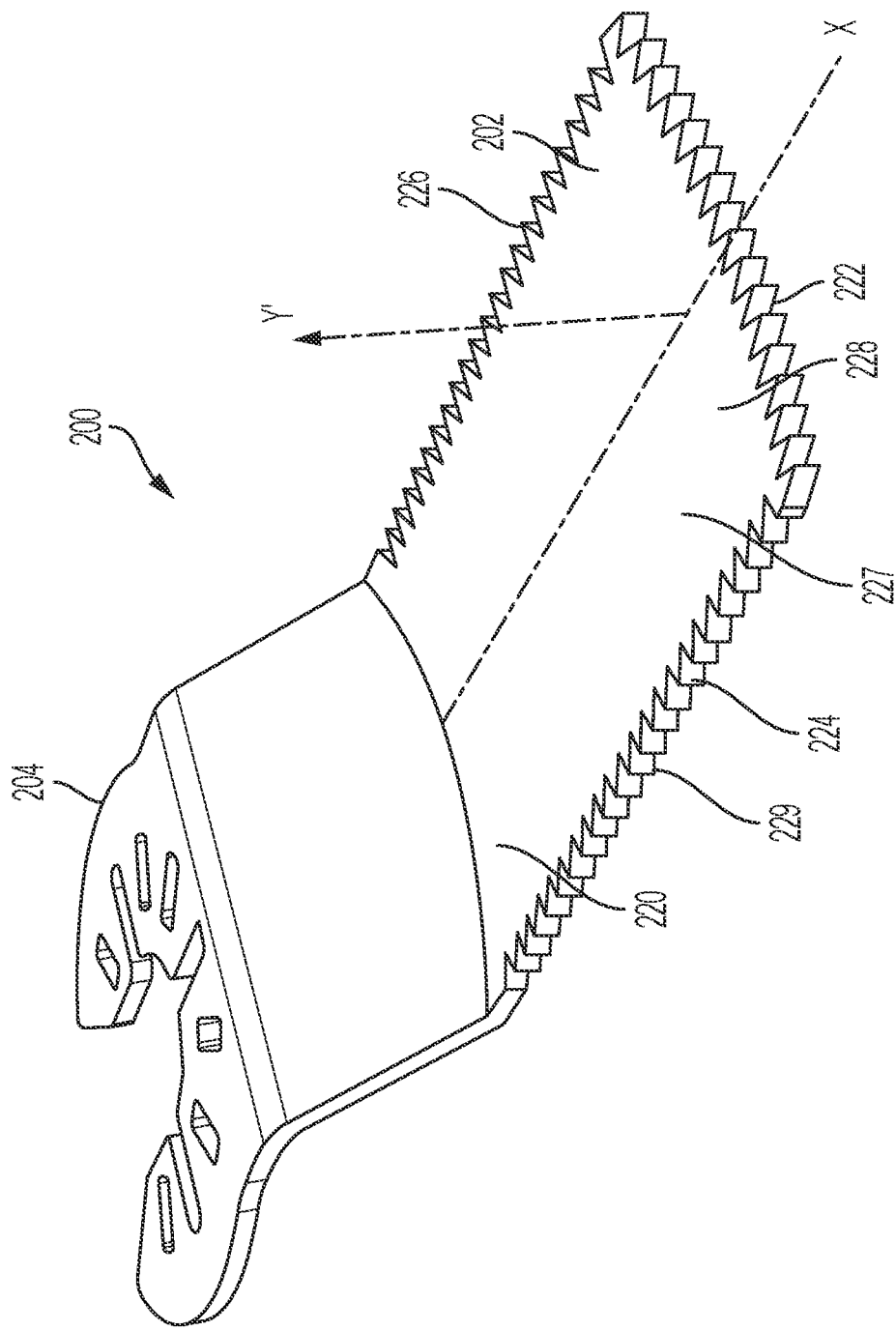
FIG. 5 is a perspective view of a second implementation of an oscillating accessory.

Referring to FIG. 5, another implementation of an oscillating accessory 200 includes a working portion 202 and an attachment portion 204, which are the same as the working portion 102 and the attachment portion 104 of the oscillating accessory 100 of FIGS. 2-4, with the following differences. The working portion 202 has a rear end portion 220 coupled to the attachment portion 204, a front cutting edge 222 opposite the rear end portion 220, a first side edge 224 extending from the front cutting edge 222 toward the rear end portion 220, a second side edge 226 opposite the first side edge 224 and extending from the front cutting edge 222 toward the rear end portion 220, and an at least partially curved surface 228 that contains the longitudinal axis X and the extends from the first side edge 224 to the second side edge 226. Unlike the at least partially curved surface 128, the at least partially curved surface 228 has a generally convex lower face 229 and a generally concave upper face 227 that faces in an upward direction Y' relative to the attachment portion 204. The remaining features of the working portion 202 may be similar or the same as the working portion 102 of the oscillating accessory 102 of FIGS. 2-4.

Figure 6:
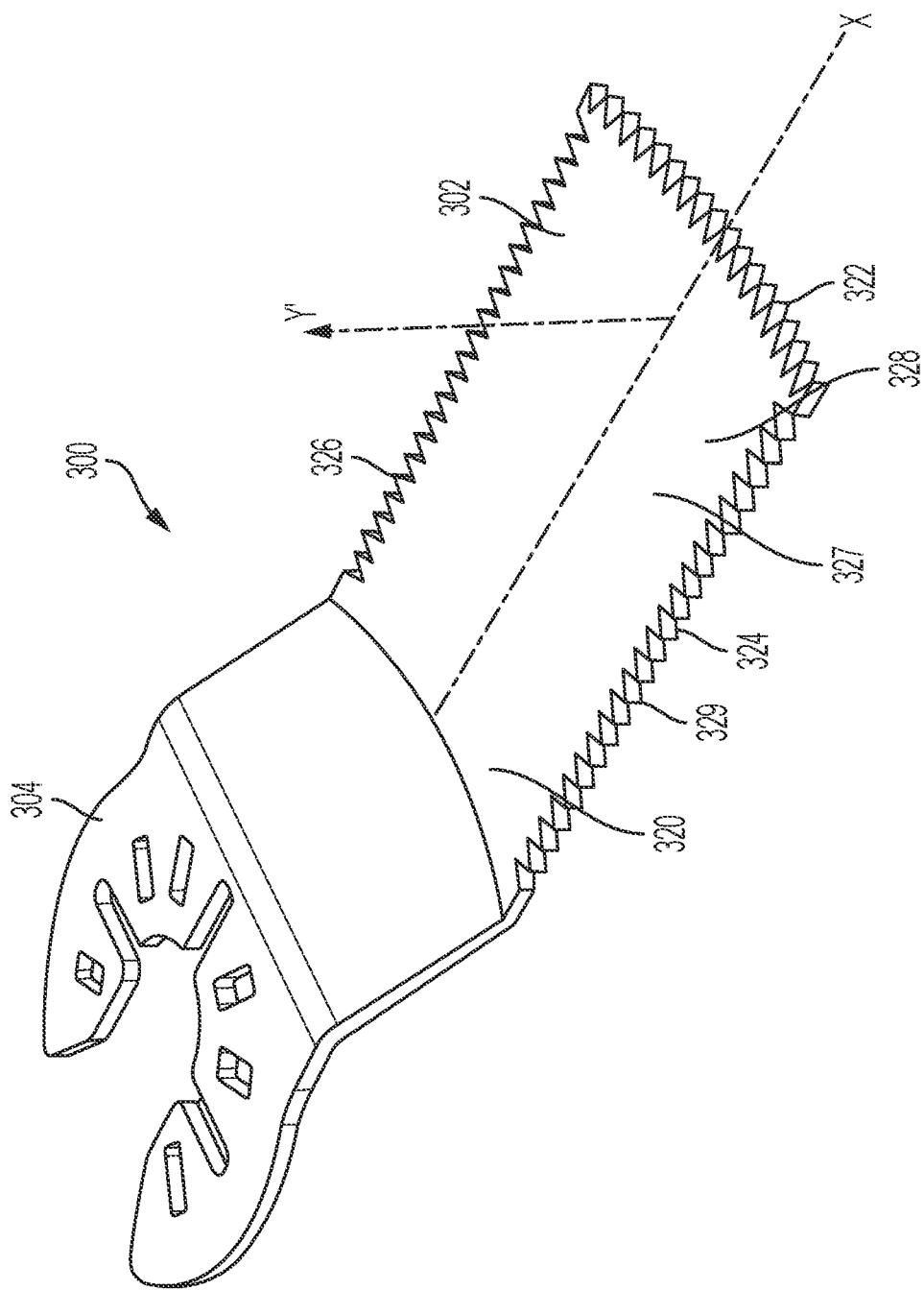
FIG. 6 is a perspective view of a third implementation of an oscillating accessory.
Figure 7:
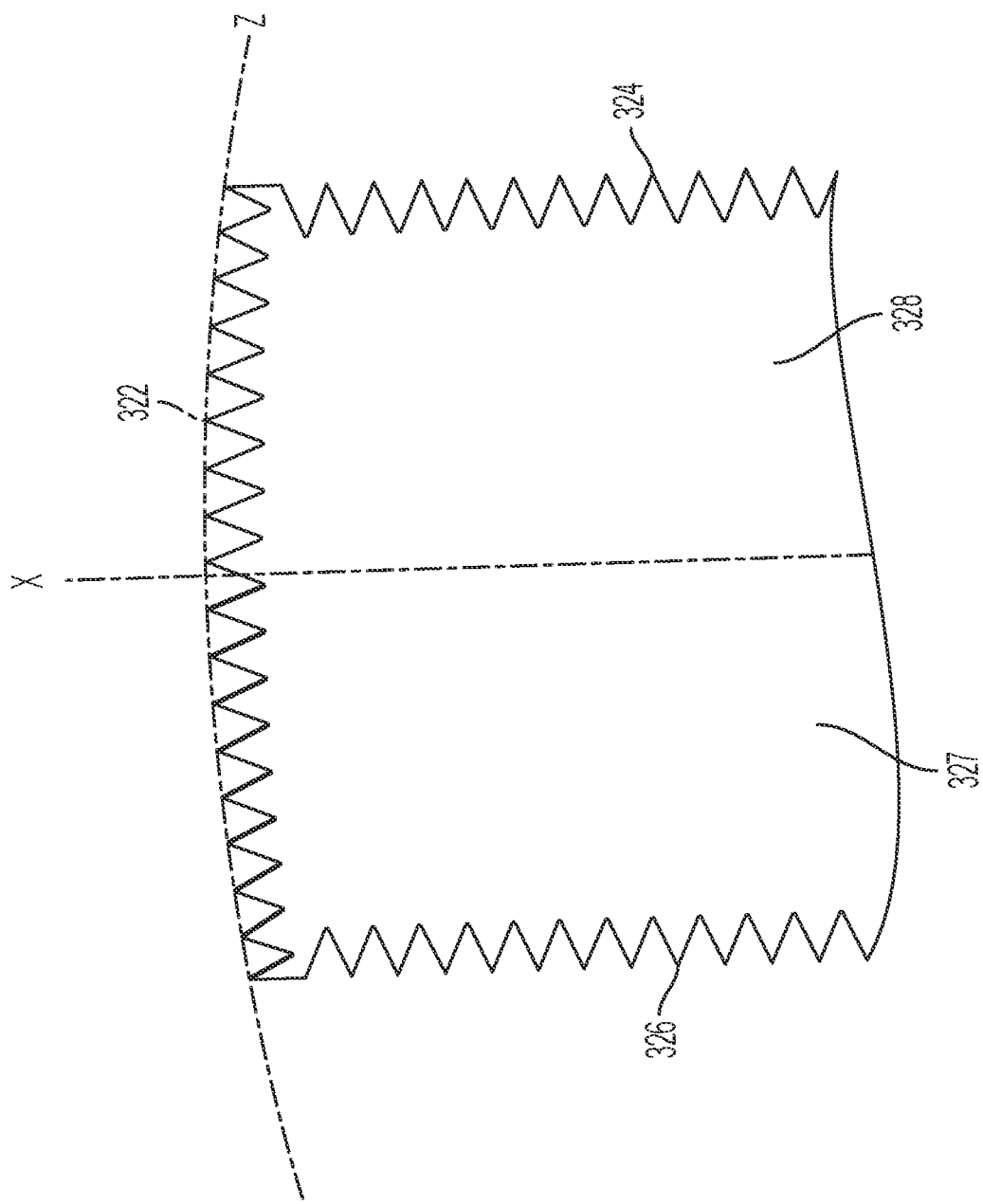
FIG. 7 is a top close up view of the front cutting edge of the accessory of FIG. 6.

Referring to FIGS. 6 and 7, another implementation of an oscillating accessory 300 includes a working portion 302 and an attachment portion 304, which are the same as the working portion 102 and the attachment portion 104 of the oscillating accessory 100 of FIGS. 2-4, with the following differences. The working portion 302 has a rear end portion 320 coupled to the attachment portion 304, a front cutting edge 322 opposite the rear end portion 320, a first side edge 324 extending from the front cutting edge 322 toward the rear end portion 320, a second side edge 326 opposite the first side edge 324 and extending from the front cutting edge 322 toward the rear end portion 320, and an at least partially curved surface 328 that contains the longitudinal axis X and the extends from the first side edge 324 to the second side edge 326. Unlike the at least partially curved surface 128, the at least partially curved surface 328 has a generally convex lower face 329 and a generally concave upper face 327 that faces in an upward direction Y' relative to the attachment portion 304. Also, unlike the front cutting edge 122 that is straight when viewed from the top, the front cutting edge 322 is curved so that tips of the teeth lie along a curve Z' when viewed from the top. The curve Z' is concave facing toward the attachment portion 302. However, it should be understood that the curve may be concave facing away from the attachment portion 302, may have an S-shaped or sine-wave shaped curvature, and/or may be partially curved and partially straight. The remaining features of the working portion 302 may be similar or the same as the working portion 102 of the oscillating accessory 102 of FIGS. 2-4.

Figure 8:
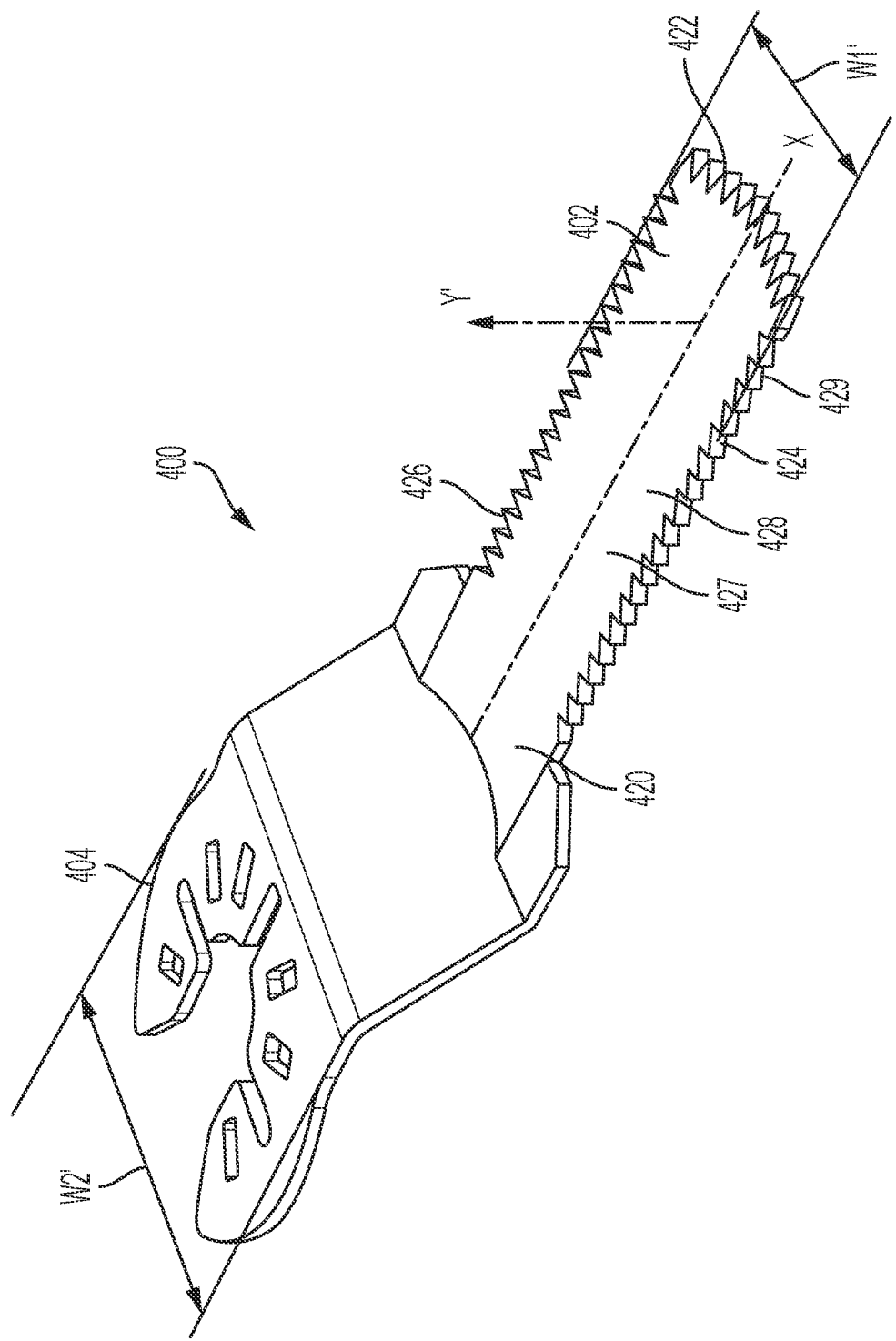
FIG. 8 is a perspective view of a fourth implementation of an oscillating accessory.

Referring to FIG. 8, another implementation of an oscillating accessory 400 includes a working portion 402 and an attachment portion 404, which are the same as the working portion 302 and the attachment portion 304 of the oscillating accessory 300 of FIGS. 6-7, with the following differences. The working portion 402 has a rear end portion 420 coupled to the attachment portion 404, a front cutting edge 422 opposite the rear end portion 420 and curved when viewed from a top of the working portion 402 in a concave direction facing toward the working portion, a first side edge 424 extending from the front cutting edge 422 toward the rear end portion 420, a second side edge 426 opposite the first side edge 424 and extending from the front cutting edge 422 toward the rear end portion 420, and an at least partially curved surface 428 that contains the longitudinal axis X, extends from the first side edge 424 to the second side edge 426, and has a concave upper face 327 facing an upward direction Y'. Unlike the working portion 302 which has a width that is approximately the same as a width of the attachment portion 304, the working portion 402 has a first width W1' that is less than a second width W2' of the attachment portion 404. It should be understood that in other embodiments, the width of the working portion may be greater than a width of the attachment portion. The remaining features of the working portion 402 may be similar or the same as the working portion 302 of the oscillating accessory 302 of FIGS. 6-7.

Figure 9:
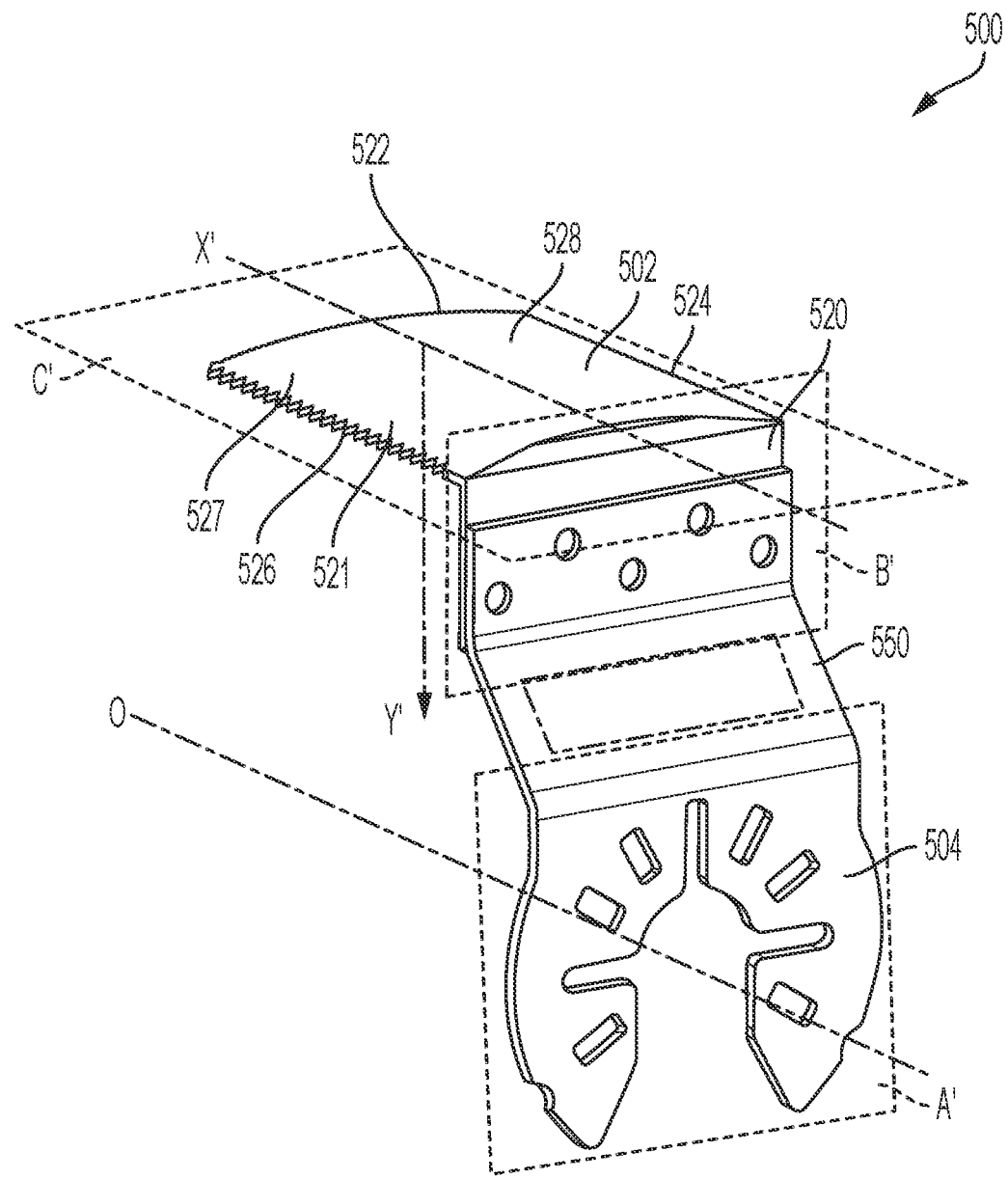
FIG. 9 is a top perspective view of a fifth implementation of an oscillating accessory.
Figure 10:
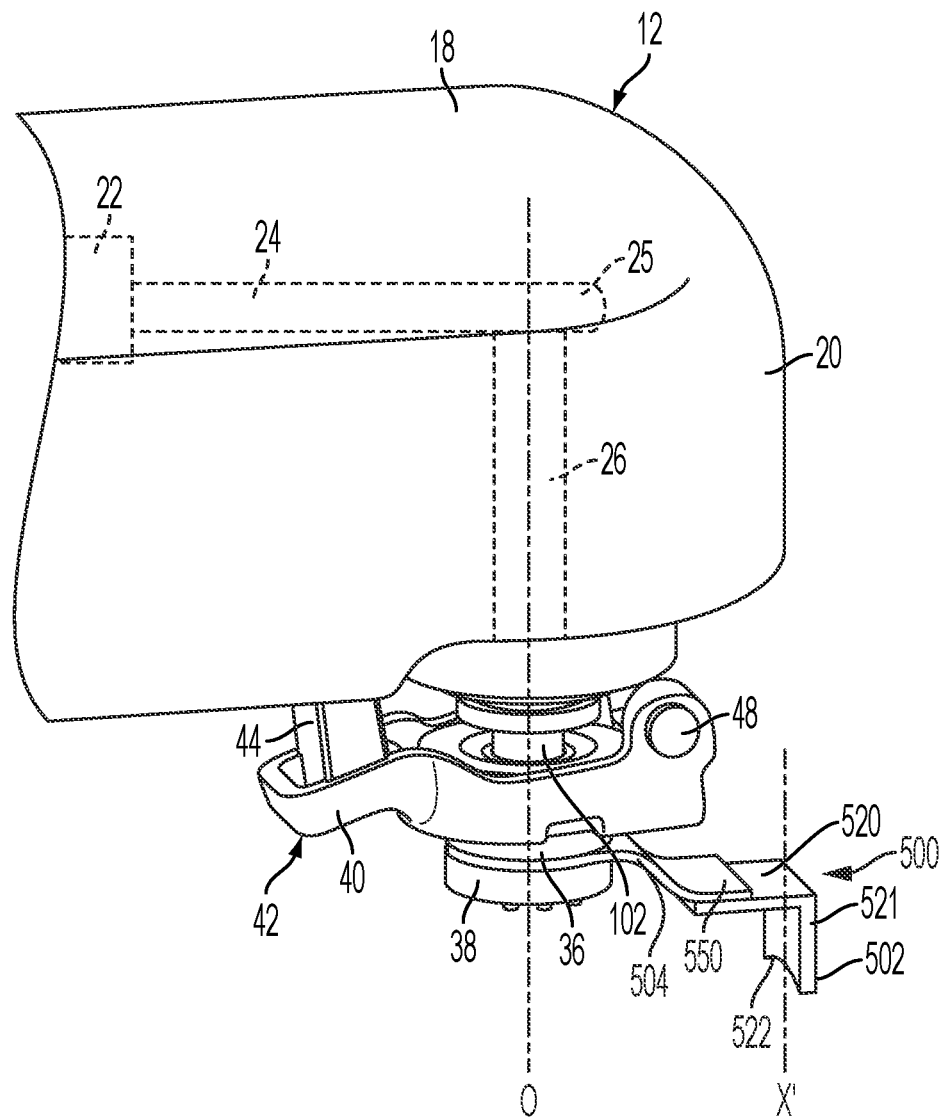
FIG. 10 is a perspective view of the accessory of FIG. 9 coupled to the oscillating power tool of FIG. 1A.
Figure 11:
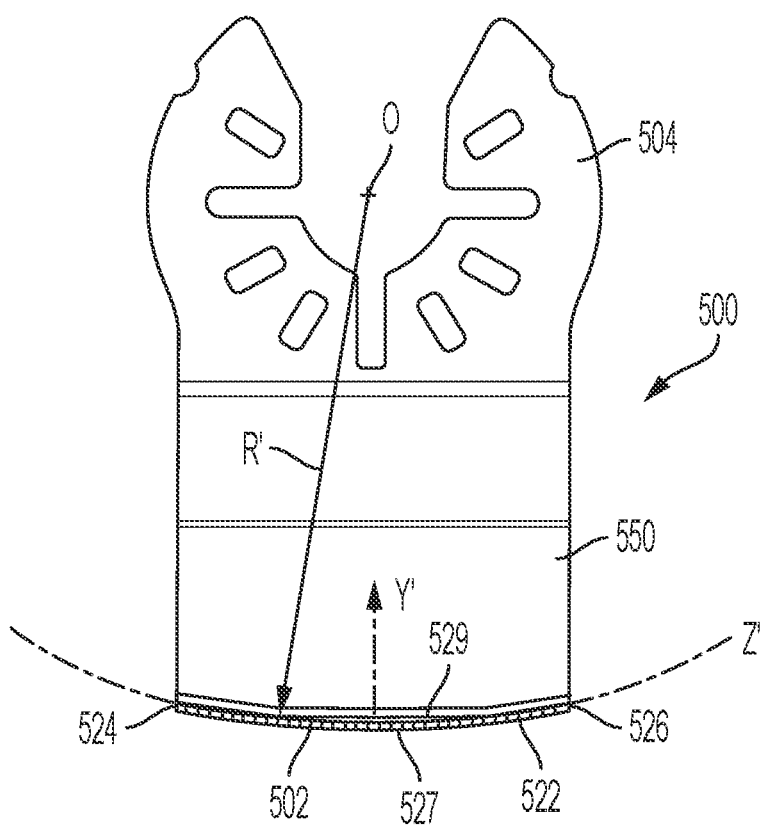
FIG. 11 is a front view of the accessory of FIG. 9.
Figure 12:
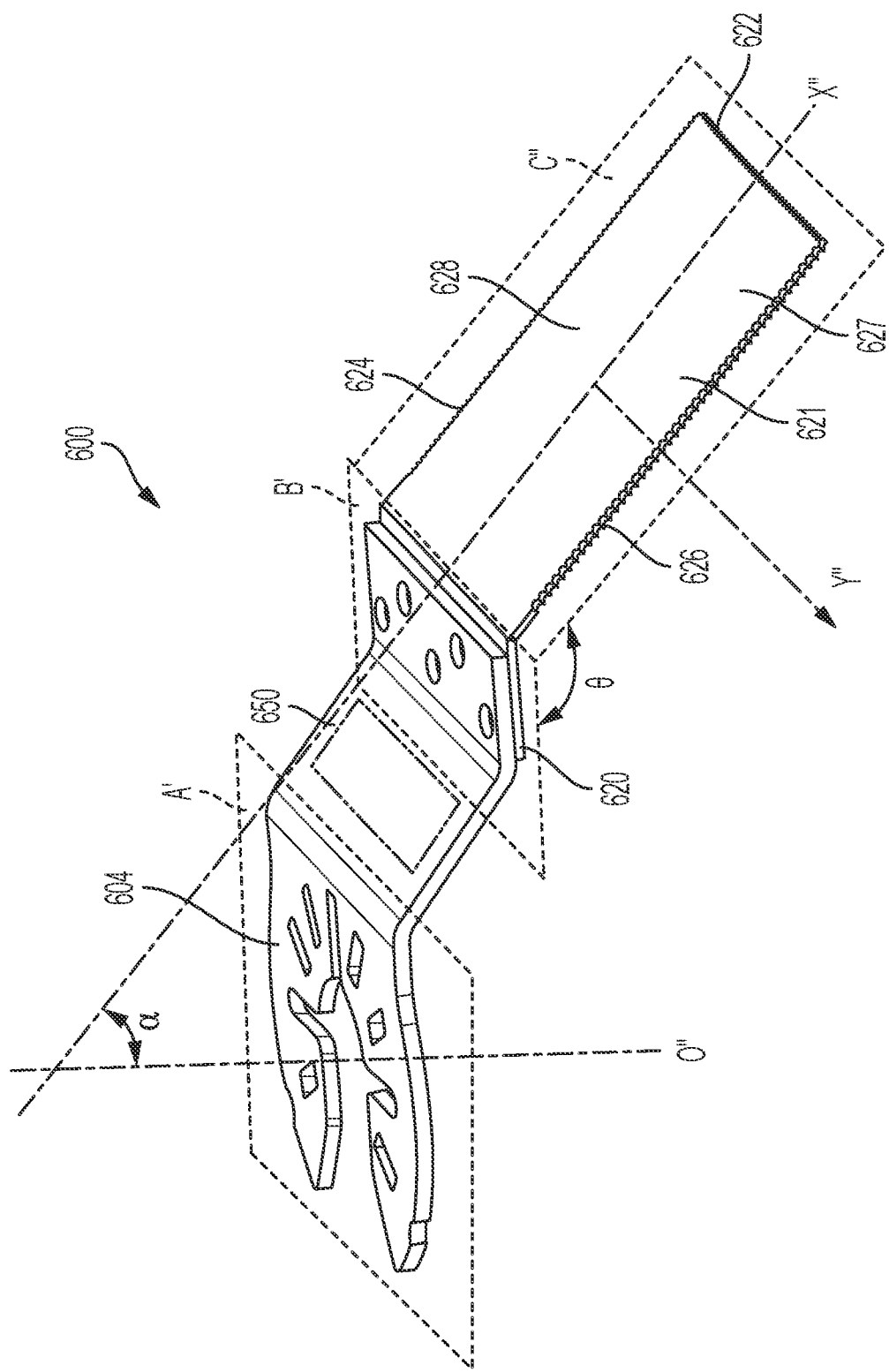
FIG. 12 is a top perspective view of a sixth implementation of an oscillating accessory.
Figure 13:
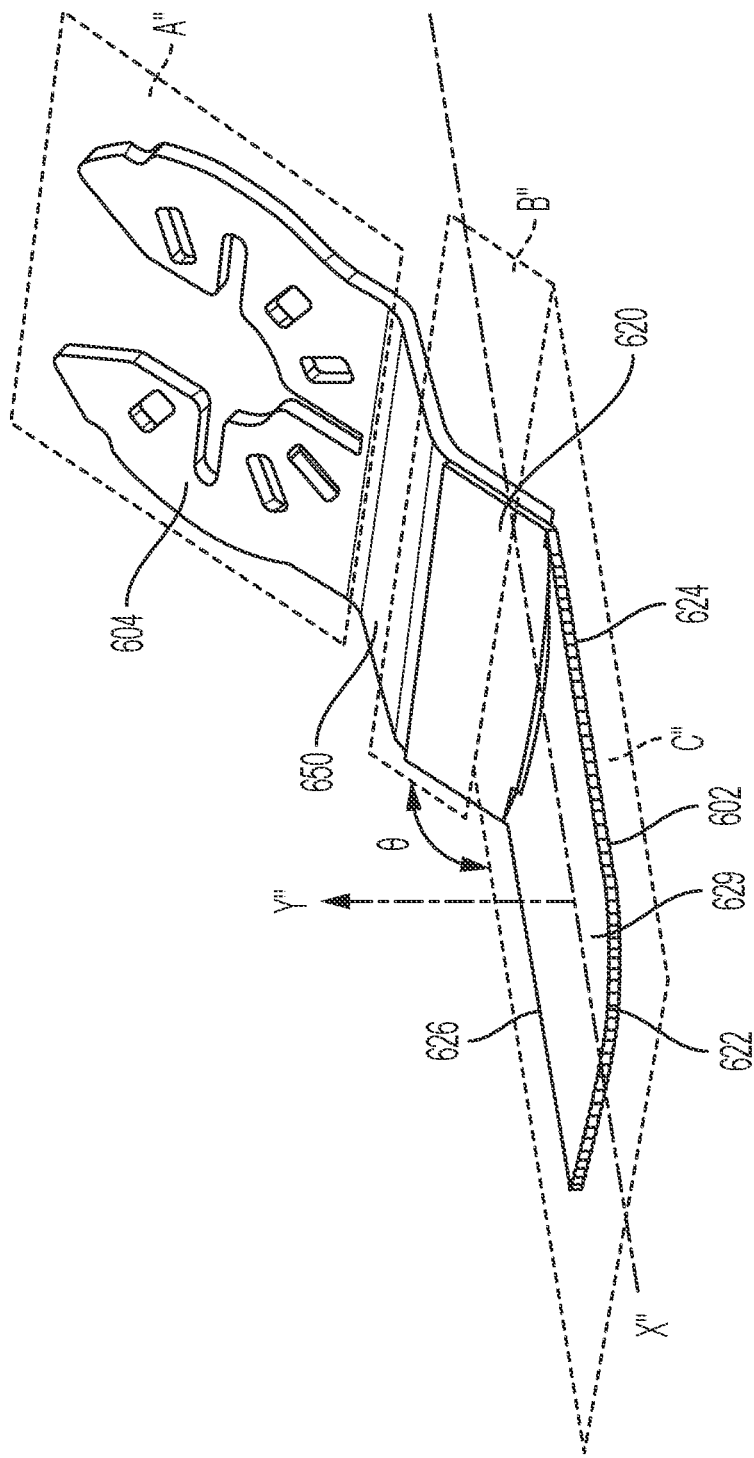
FIG. 13 is a bottom perspective view of the accessory of FIG. 12.

Referring to FIGS. 9-11, another implementation of an oscillating accessory 500 includes a working portion 502 and an attachment portion 504, which are similar to the working portion 102 and the attachment portion 104 of the oscillating accessory 100 of FIGS. 2-4, with the following differences. The attachment portion 504 includes a generally planar portion 505 lying generally in a first plane A'. The working portion 502 includes a rear planar portion 520 coupled to the attachment portion 504 and a front curved portion 521 that is generally perpendicular to the rear planar portion 520.

In the illustrated implementation, the rear planar portion 520 lies in a second plane B' and is coupled to the attachment portion 504 via an intermediate portion 550 that is substantially similar to the intermediate portion 150 of the oscillating accessory 100 of FIGS. 2-4. The intermediate portion 550 may disposed at a right angle or an acute angle (e.g., approximately 15° to approximately 89°) to the attachment portion 504. Thus, the second plane B' is generally parallel to and offset from the first plane A'. This offset may make it easier for the working portion 502 to plunge deeper into a workpiece without interference from the clamp assembly 30 on the oscillating power tool 12. In other implementations, the rear planar portion 550 may be coupled directly to the attachment portion 550 and the second plane B' may be substantially co-planar with the first plane A' (or they may have portions that are substantially co-planar) or may substantially lie (or have portions that substantially lie) in planes that are at an angle to one another. It will be understood to one of ordinary skill in the art that the attachment portion 504 may not be planar but instead may have portions that substantially lie in or along a plane.

The front curved portion 520 of the working portion 502 extends generally along a longitudinal axis X' that is transverse (e.g., generally perpendicular) to the first plane A' and the second plane B'. The front curved portion 521 includes a front cutting edge 522 opposite the rear end portion 520, a first side edge 524 (which may be a cutting edge or a non-cutting edge) extending from the front cutting edge toward the rear end portion 520, and a second side edge 526 (which may be a cutting edge or a non-cutting edge) opposite the first side edge 524 and extending from the front cutting edge 522 toward the rear end portion 520. The front curved portion 521 includes an at least partially curved surface 528 that contains the longitudinal axis X' and the extends from the first side edge 524 to the second side edge 526. At the longitudinal axis X', the at least partially curved surface 528 is tangent to a third plane C' that is transverse (e.g., generally perpendicular) to the first plane A' and that contains the longitudinal axis X'. The at least partially curved surface 528' has a generally convex upper face 527' and a generally concave lower face 529' that faces in a direction Y' that is parallel to the first plane A' of the attachment portion 504 and that extends in the same direction as the attachment portion 504. The front cutting edge 522 is curved so that tips of its teeth lie along a curve Z' that is concave facing in the same direction as the attachment portion 504.

As shown in FIG. 10, the longitudinal axis X' along which the curved portion 521 of the working portion 502 extends is generally parallel to an oscillating axis O about which the working portion 504 oscillates when the accessory 500 is coupled to an oscillating power tool (such as the oscillating power tool 12 shown in FIG. 1A). As shown in FIG. 11, the front cutting edge 522 may have a radius of curvature R' that is centered at the oscillating axis O. In other implementations, the radius of curvature may be centered at a point that is offset rearward or frontward of the oscillating axis O. Having the curved portion 521 of the working portion 502 extend generally parallel to the oscillating axis O helps facilitate cutting circular or rounded openings in a workpiece since the curved cutting edge 522 will oscillate about the oscillating axis O. The remaining features of the oscillating accessory may be similar to or the same as the oscillating accessory 100 of FIGS. 2-4.

Referring to FIGS. 12-15, another implementation of an oscillating accessory 600 includes a working portion 602 and an attachment portion 604, which are similar to the working portion 502 and the attachment portion 504 of the oscillating accessory 500 of FIGS. 9-11, with the following differences. The attachment portion 604 includes a generally planar portion 605 lying generally in a first plane A". The working portion 602 includes a rear planar portion 620 coupled to the attachment portion 604 and a front curved portion 621 that is at an obtuse angle θ to the rear planar portion 620.

In the illustrated implementation, the rear planar portion 620 lies in a second plane B" and is coupled to the attachment portion 604 via an intermediate portion 650 that is substantially similar to the intermediate portion 550 of the oscillating accessory 500. The intermediate portion 650 may disposed at a right angle or an acute angle (e.g., approximately 15° to approximately 89°) to the attachment portion 604. Thus, the second plane B" is generally parallel to and offset from the first plane A". This offset may make it easier for the working portion 602 to plunge deeper into a workpiece without interference from the clamp assembly 30 on the oscillating power tool 12. In other implementations, the rear planar portion 650 may be coupled directly to the attachment portion 650 and the second plane B" may be substantially co-planar with the first plane A" (or they may have portions that are substantially co-planar) or may substantially lie (or have portions that substantially lie) in planes that are at an angle to one another. It will be understood to one of ordinary skill in the art that the attachment portion 604 may not be planar but instead may have portions that substantially lie in or along a plane.

The front curved portion 628 of the working portion 602 extends generally along a longitudinal axis X" that is transverse (e.g., at the obtuse angle θ) to the first plane A" and the second plane B". The obtuse angle θ may be, e.g., approximately 120° to approximately 150° (such as approximately 135°). The front curved portion 621 includes a front cutting edge 622 opposite the rear end portion 620, a first side edge 624 (which may be a cutting edge or a non-cutting edge) extending from the front cutting edge toward the rear end portion 620, and a second side edge 626 (which may be a cutting edge or a non-cutting edge) opposite the first side edge 624 and extending from the front cutting edge 622 toward the rear end portion 620. The front curved portion 621 includes an at least partially curved surface 628 that contains the longitudinal axis X" and the extends from the first side edge 624 to the second side edge 626. At the longitudinal axis X", the at least partially curved surface 628 is tangent to a third plane C" that is transverse (e.g., at the obtuse angle θ) to the first plane A" and that contains the longitudinal axis X". The at least partially curved surface 628 has a generally convex upper face 627 and a generally concave lower face 629 that faces in a direction Y" that is at an acute angle to the first plane A" and that extends toward the attachment portion 604. The front cutting edge 622 is curved so that tips of its teeth lie along a curve Z" that is concave.

Figure 14:
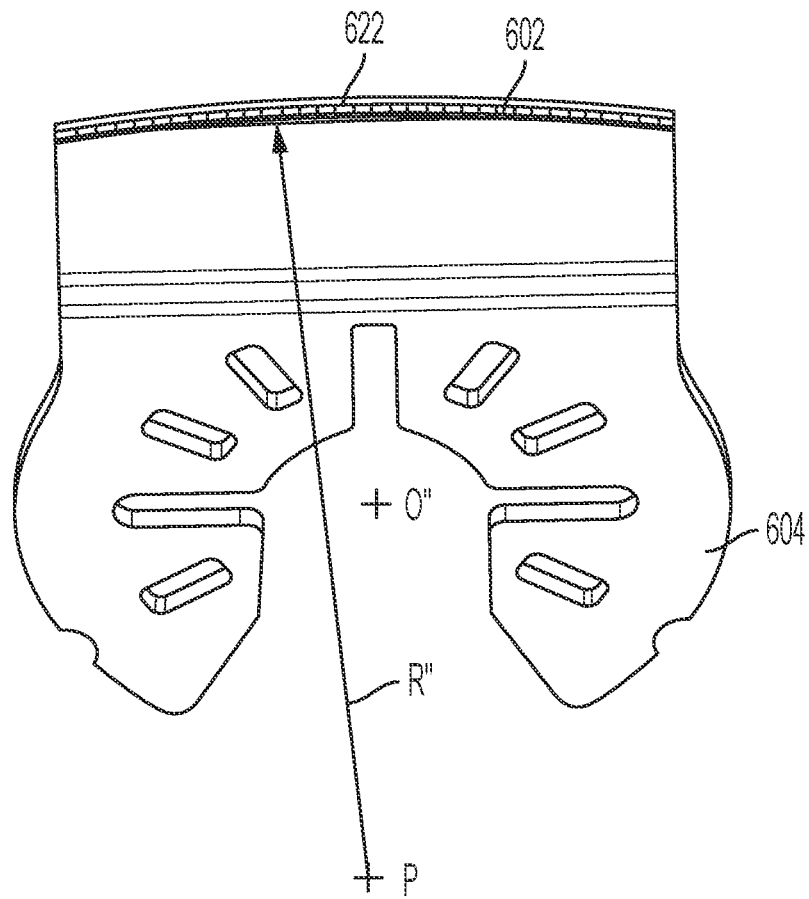
FIG. 14 is a front view of the accessory of FIG. 12.
Figure 15:
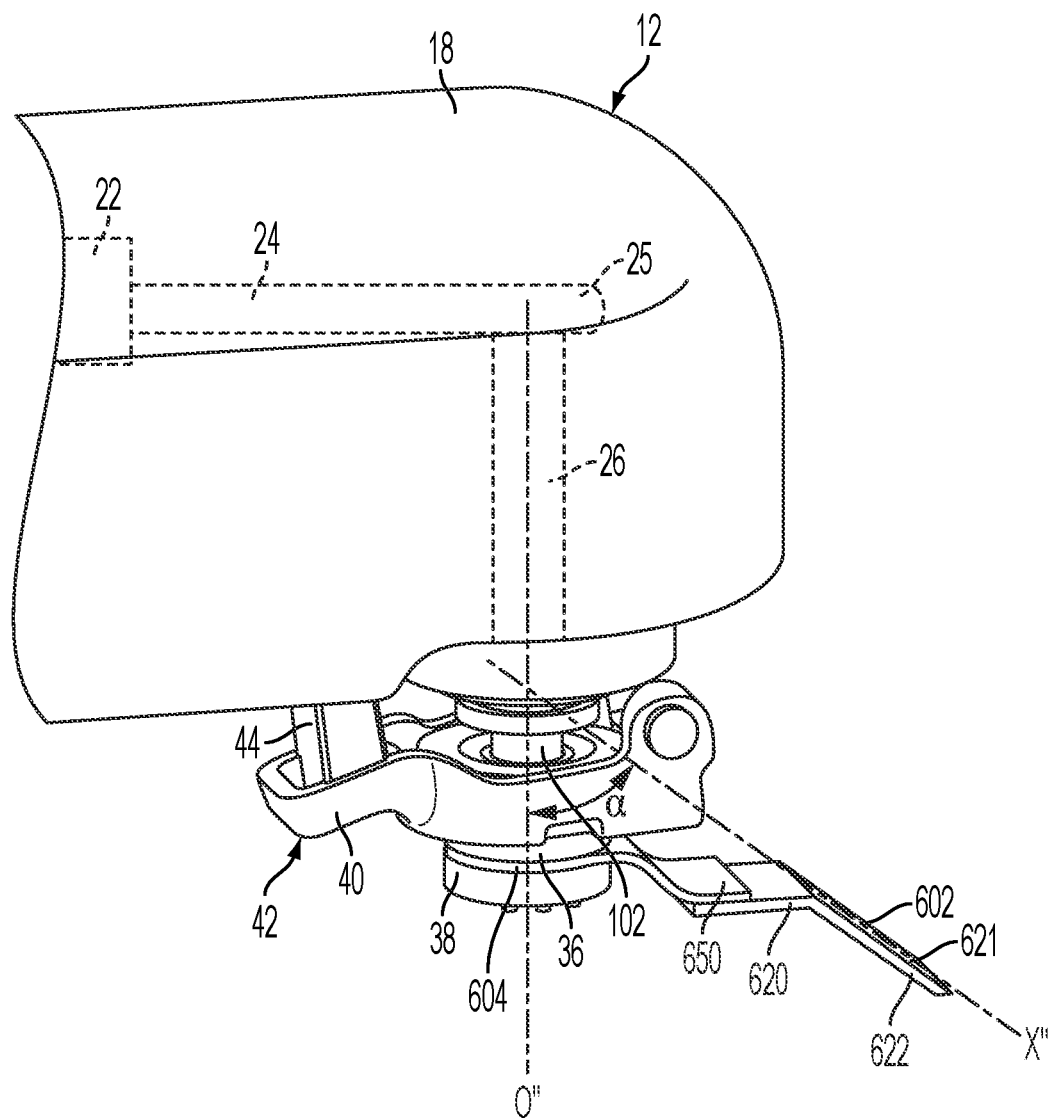
FIG. 15 is a perspective view of the accessory of FIG. 12 coupled to the oscillating power tool of FIG. 1A.

As shown in FIG. 15, the longitudinal axis X" along which the curved portion 621 of the working portion 602 extends is transverse (e.g., at an acute angle α) to an oscillating axis O" about which the working portion 604 oscillates when the accessory 600 is coupled to an oscillating power tool (such as the oscillating power tool 12 shown in FIG. 1A). The acute angle α may be, e.g., approximately 30° to approximately 60°, such as approximately 45°. As shown in FIG. 14, the front cutting edge 622 may have a radius of curvature R' that is centered at a point P rearward of the oscillating axis O". In other implementations, the radius of curvature may be centered at a point that is coincident with or frontward of the oscillating axis O". Having the curved portion 621 of the working portion 602 extend at an acute angle to the oscillating axis O" helps facilitate cutting elliptical or rounded openings in a workpiece since the curved cutting edge 622 will oscillate about the oscillating axis O". The remaining features of the oscillating accessory may be similar to or the same as the oscillating accessory 500 of FIGS. 9-11.

Referring to FIGS. 16-21, another implementation of an oscillating accessory 700 includes a working portion 702, an attachment portion 704, and an intermediate portion 750, which are similar to the working portion 502, the attachment portion 504, and the intermediate portion 550 of the oscillating accessory 500 of FIGS. 9-11, with the following differences. Like the attachment portion 504, the attachment portion 704 includes a generally planar portion 705 lying generally in a first plane A'. Like the working portion 502, the working portion 702 includes a rear planar portion 720 that lies in a second plane B' parallel to the first plane A' and a front curved portion 721 that extends a longitudinal axis X' that is transverse (e.g., generally perpendicular) to the first plane A' and the second plane B' and that is generally parallel to the oscillating axis O' about which the working portion 704 oscillates when the accessory 700 is coupled to an oscillating power tool.

Like the front curved portion 521, the front curved portion 721 includes a front cutting edge 722 opposite the rear end portion 720, a first side edge 724 (which may be a cutting edge or a non-cutting edge) extending from the front cutting edge toward the rear end portion 720, and a second side edge 726 (which may be a cutting edge or a non-cutting edge) opposite the first side edge 724 and extending from the front cutting edge 722 toward the rear end portion 720. The front curved portion 721 includes an at least partially curved surface 728 that contains the longitudinal axis X' and the extends from the first side edge 724 to the second side edge 726. At the longitudinal axis X', the at least partially curved surface 728 is tangent to a third plane C' that is transverse (e.g., generally perpendicular) to the first plane A' and that contains the longitudinal axis X'. The at least partially curved surface 728 has a generally convex upper face 727 and a generally concave lower face 729 that faces in a direction Y' that is parallel to the first plane A' of the attachment portion 704 and that extends in the same direction as the attachment portion 704. The front cutting edge 722 is curved so that tips of its teeth lie along a curve C that is concave facing in the same direction as the attachment portion 704.

Figure 16:
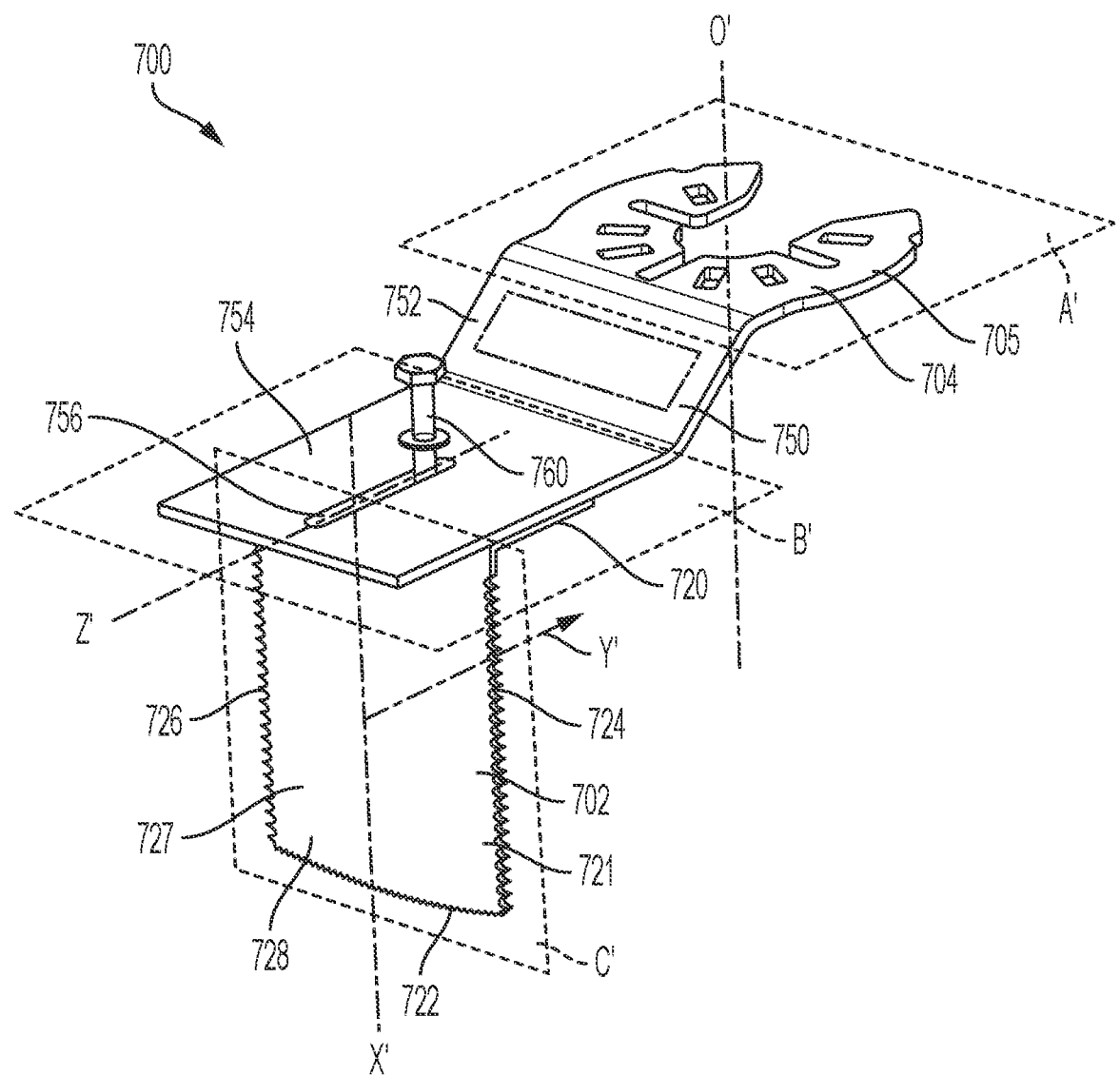
FIG. 16 is a top perspective view of a seventh implementation of an oscillating accessory, shown in a first position.
Figure 17:
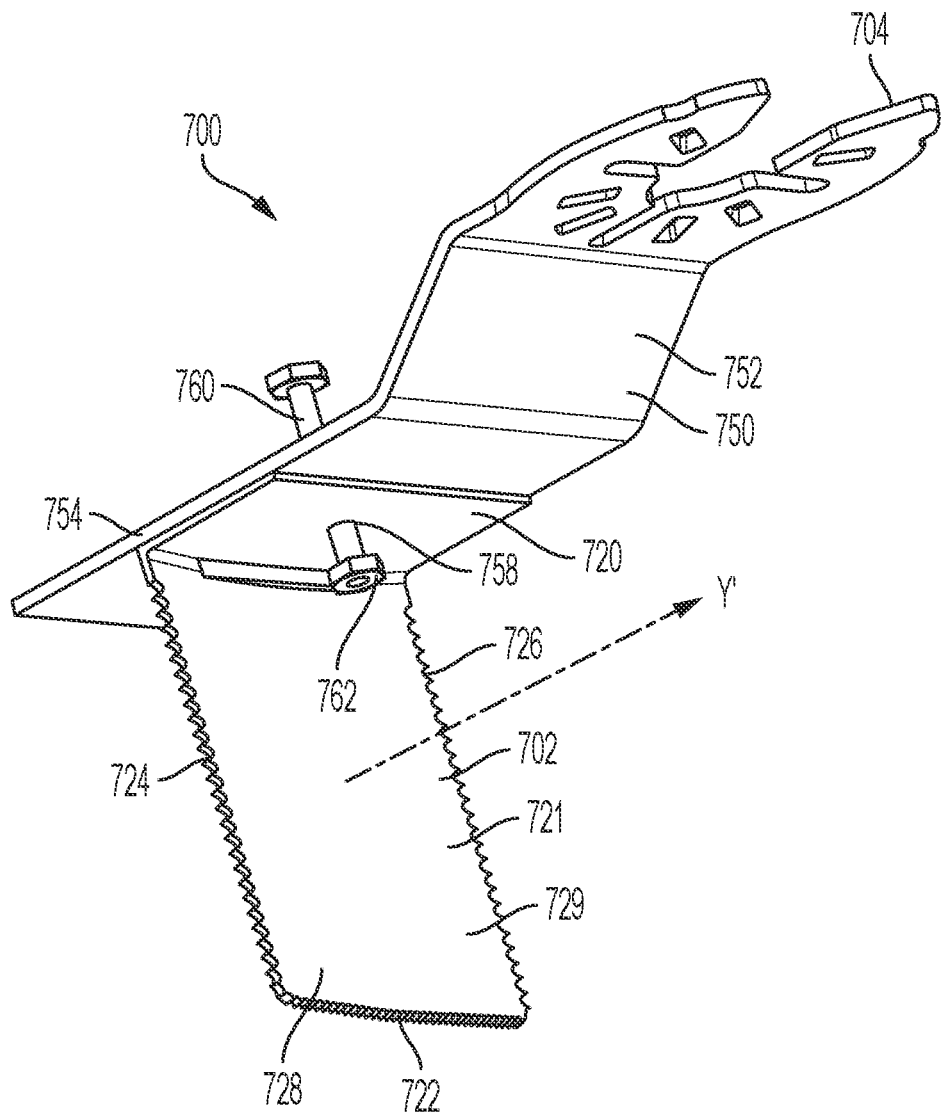
FIG. 17 is a bottom perspective view of the accessory of FIG. 16, shown in the first position.
Figure 18:
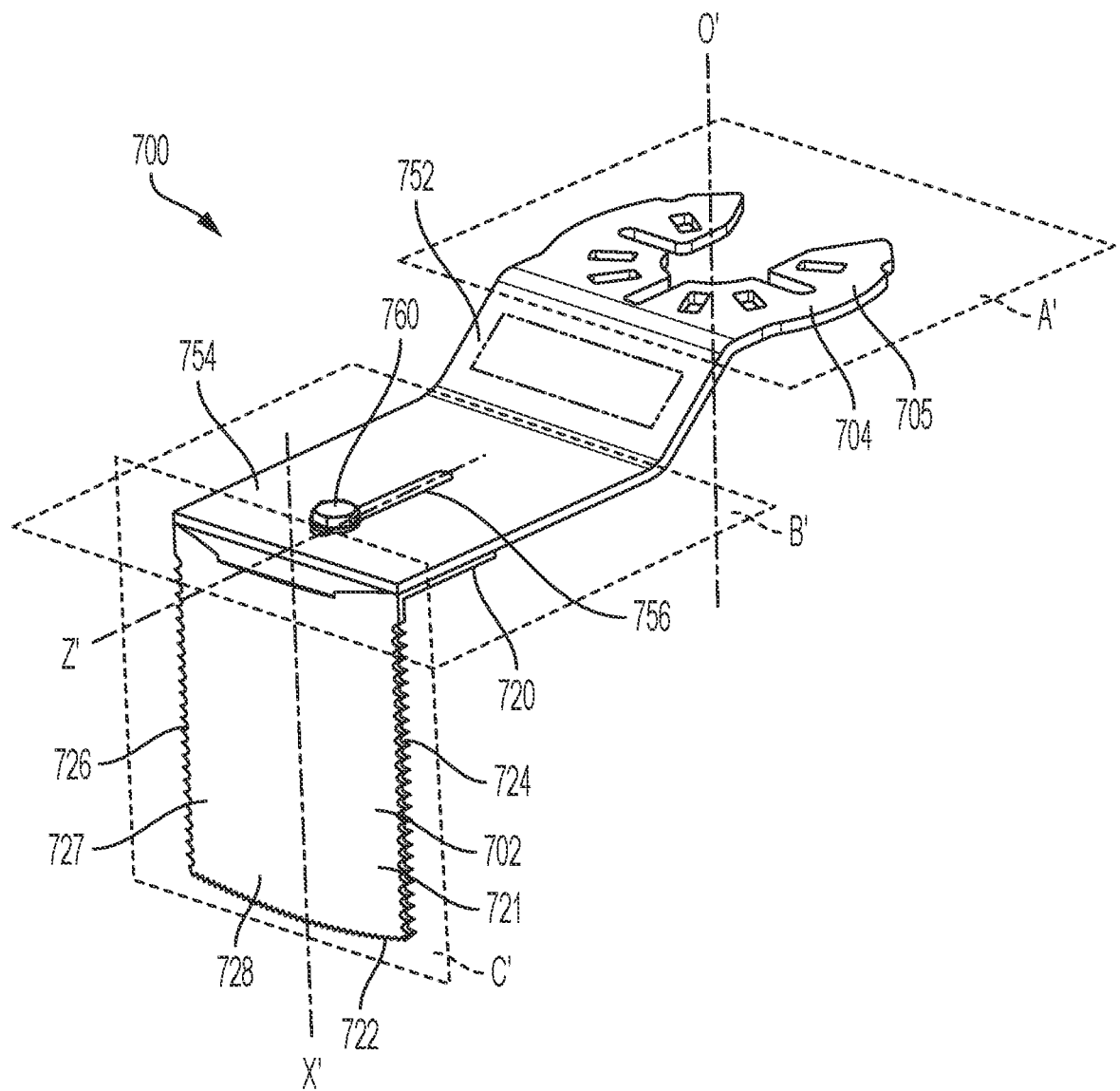
FIG. 18 is a top perspective view of the accessory of FIG. 16, shown in a second position.
Figure 19:
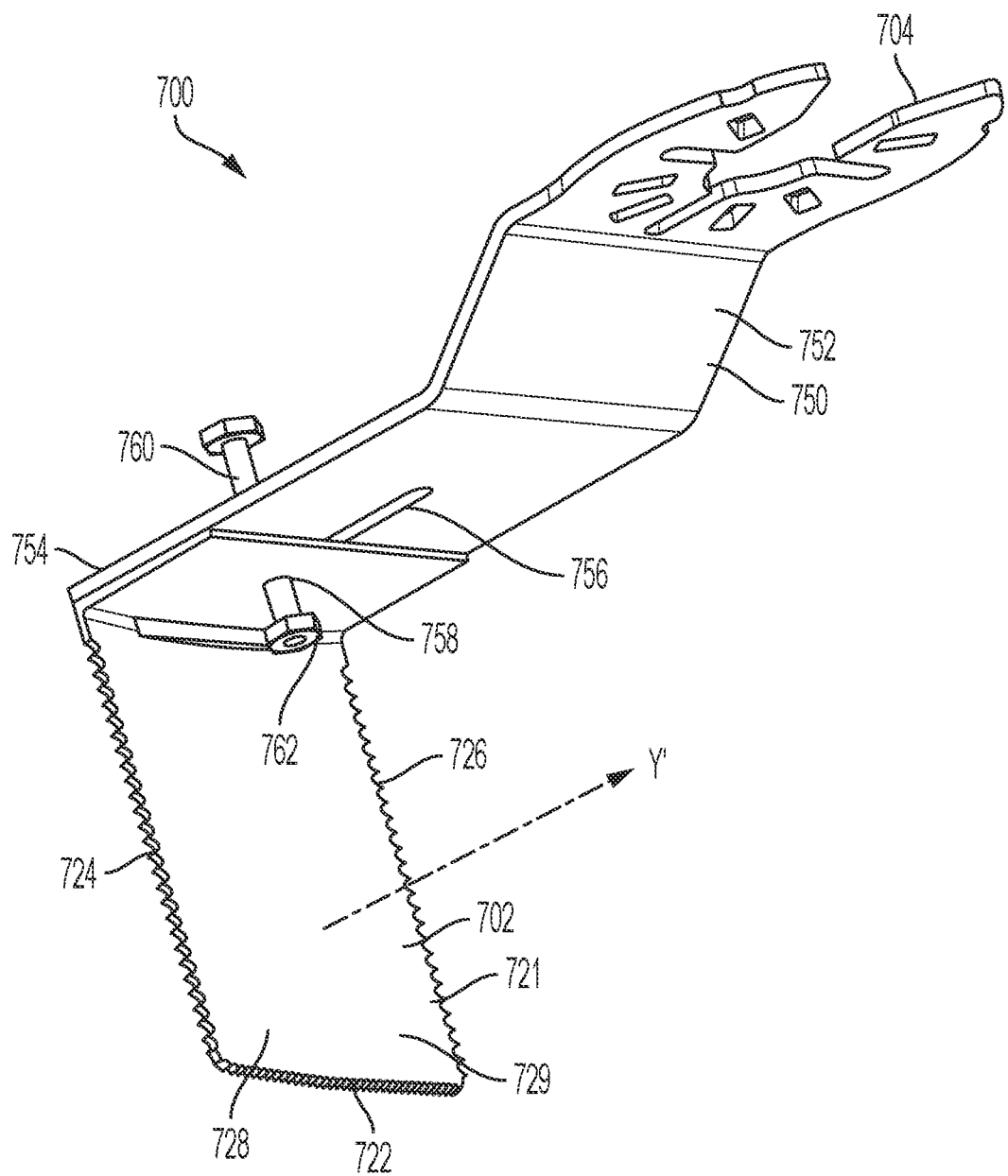
FIG. 19 is a bottom perspective view of the accessory of FIG. 16, shown in the second position.
Figure 20:
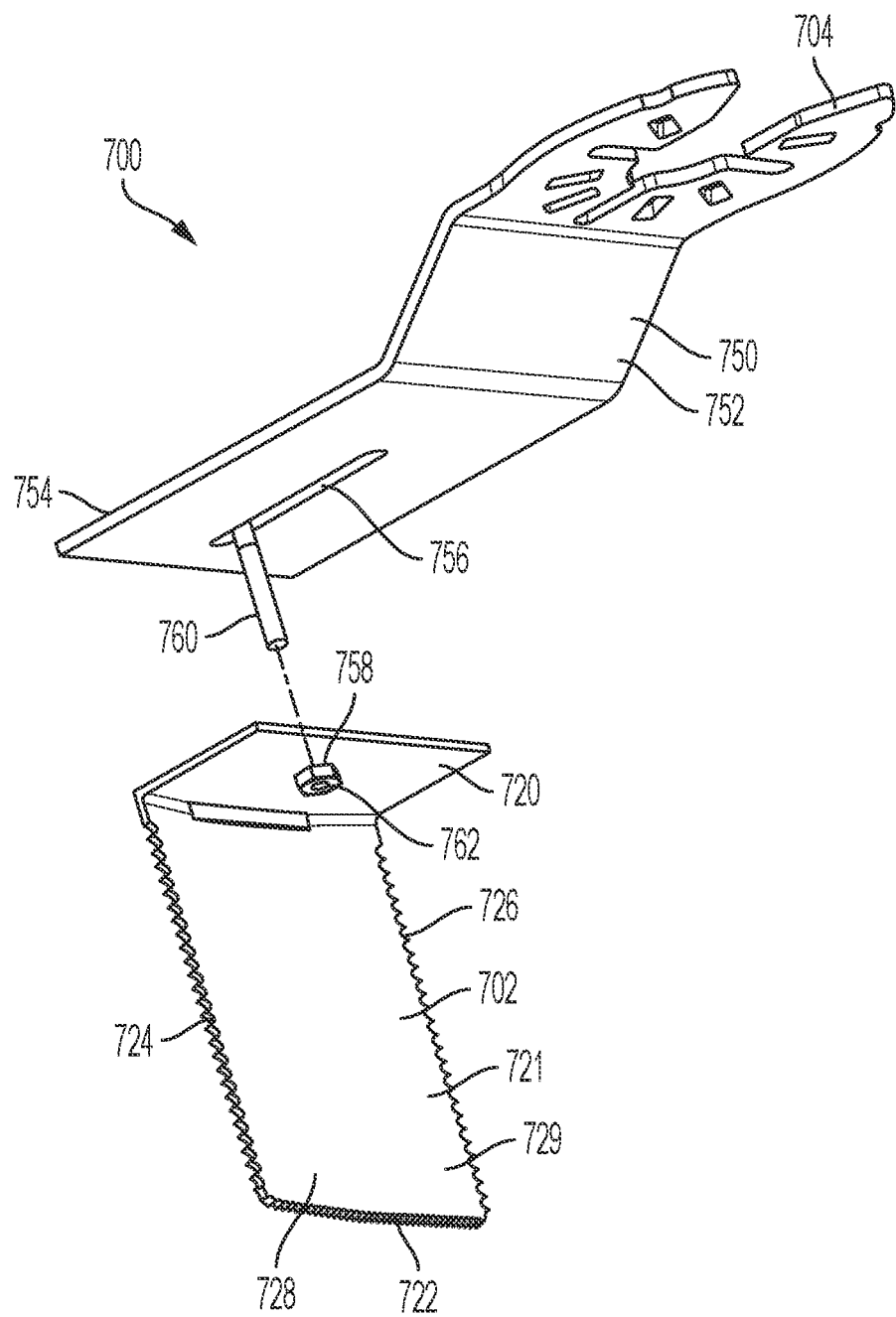
FIG. 20 is an exploded bottom perspective view of the accessory of FIG. 16.
Figure 21:
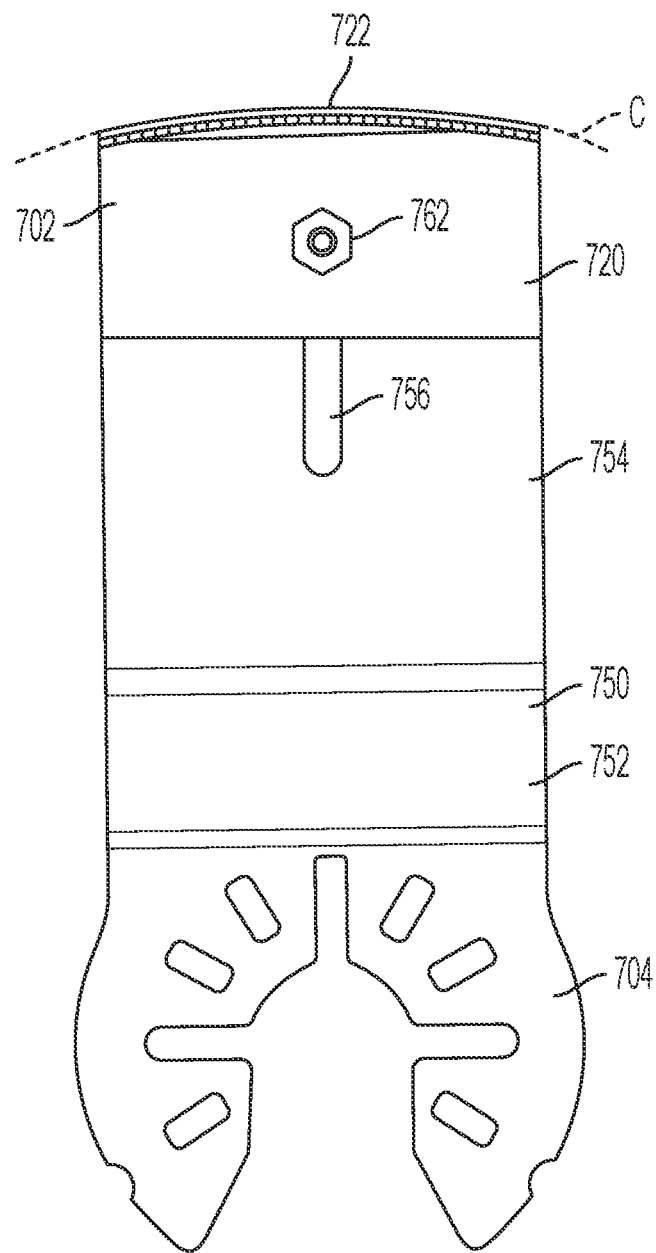
FIG. 21 is a front view of the accessory of FIG. 16.

Unlike the oscillating accessory 500, the intermediate portion 750 of the oscillating accessory 700 includes an angled surface 752 at that extends from and is transverse to the first plane A' and a horizontal surface 754 that is generally parallel to the first plane A', such that the horizontal surface is offset from the attachment portion 704. The horizontal surface 754 defines an axial slot 756 therethrough that extends along an axis Z' that is parallel to the first plane A'. The horizontal surface 754 abuts against the rear end portion 720 of the working portion 702. The rear end portion 720 defines an opening 758 therethrough. A threaded bolt 760 is received through the axial slot 756 and the opening 758 and a nut 762 may be threaded into the bolt 760 and tightened to releasably secure the working portion 702 to the intermediate portion 750. When the nut 762 is loosened, the threaded bolt 760 can be moved along the axial slot 702, causing the working portion 702 to move between a rearmost position closer to the attachment portion 702 (as shown in FIGS. 16 and 17) and a forwardmost position further from the attachment portion 702 (as shown in FIGS. 18 and 19). This enables the adjustment of the position of the working portion 702 relative to the attachment portion 704 along the axis Z' in any number of positions between the rearmost and forwardmost positions. In an implementation, the threaded bolt 760 may be integral with the working portion 702. In another implementation, the threaded bolt 760 and the opening 758 in the working portion 702 may have a non-circular (e.g., double-D shaped) cross-section to inhibit pivoting movement between the working portion 702 and the intermediate portion 750. In yet other implementations, the intermediate portion 750 may have a plurality of slots and the working portion 702 may have a plurality of openings that receive a plurality of threaded bolts therethrough. In another implementation, the axial slot may be defined in the working portion and the opening may be defined in the intermediate portion.

Referring to FIGS. 22-27, another implementation of an oscillating accessory 800 includes a working portion 802, an attachment portion 804, and an intermediate portion 850, which are similar to the working portion 602, the attachment portion 604, and the intermediate portion 650 of the oscillating accessory 500 of FIGS. 12-15, with the following differences. Like the attachment portion 604, the attachment portion 804 includes a generally planar portion 805 lying generally in a first plane A'. Like the working portion 602, the working portion 802 includes a rear planar portion 820 that lies in a second plane B' parallel to the first plane A' and a front curved portion 821 that extends along a longitudinal axis X' that is transverse (e.g., at an obtuse angle θ (e.g., approximately 120° to approximately 150°, such as approximately 135°)) to the first plane A' and the second plane B' and that is transverse (e.g., at an acute angle α (e.g., approximately 30° to approximately 60°, such as approximately 45°) to the oscillating axis O' about which the working portion 804 oscillates when the accessory 800 is coupled to an oscillating power tool.

Like the front curved portion 621, the front curved portion 821 includes a front cutting edge 822 opposite the rear end portion 820, a first side edge 824 (which may be a cutting edge or a non-cutting edge) extending from the front cutting edge toward the rear end portion 820, and a second side edge 826 (which may be a cutting edge or a non-cutting edge) opposite the first side edge 824 and extending from the front cutting edge 822 toward the rear end portion 820. The front curved portion 821 includes an at least partially curved surface 828 that contains the longitudinal axis X' and the extends from the first side edge 824 to the second side edge 826. At the longitudinal axis X', the at least partially curved surface 828 is tangent to a third plane C' that is transverse (e.g., at an obtuse angle) to the first plane A' and that contains the longitudinal axis X'. The at least partially curved surface 828 has a generally convex upper face 827 and a generally concave lower face 829 that faces in a direction Y' that extends generally toward the attachment portion 804. The front cutting edge 822 is curved so that tips of its teeth lie along a curve C that is concave facing in the same direction as the attachment portion 804.

Figure 22:
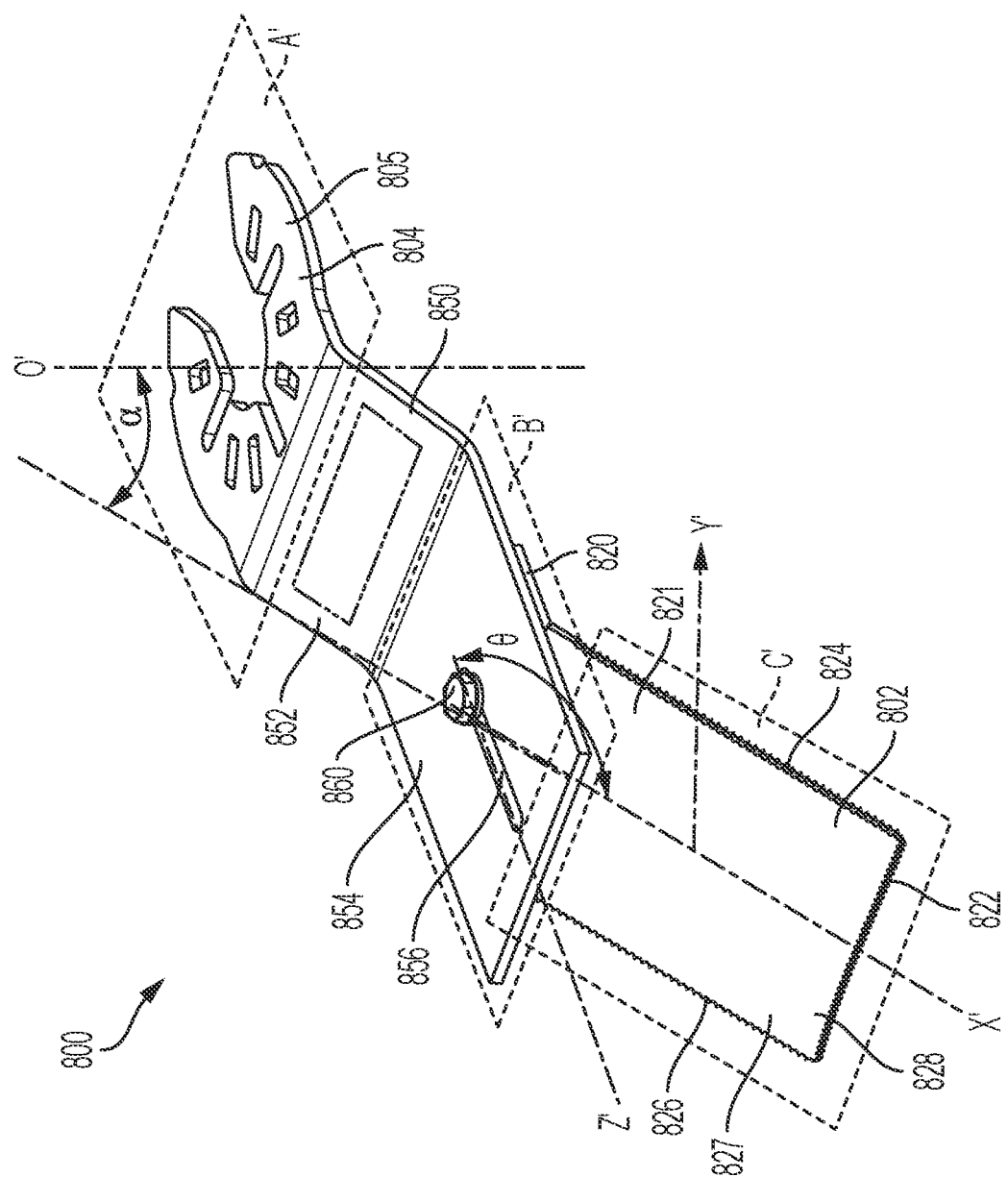
FIG. 22 is a top perspective view of an eighth implementation of an oscillating accessory, shown in a first position.
Figure 23:
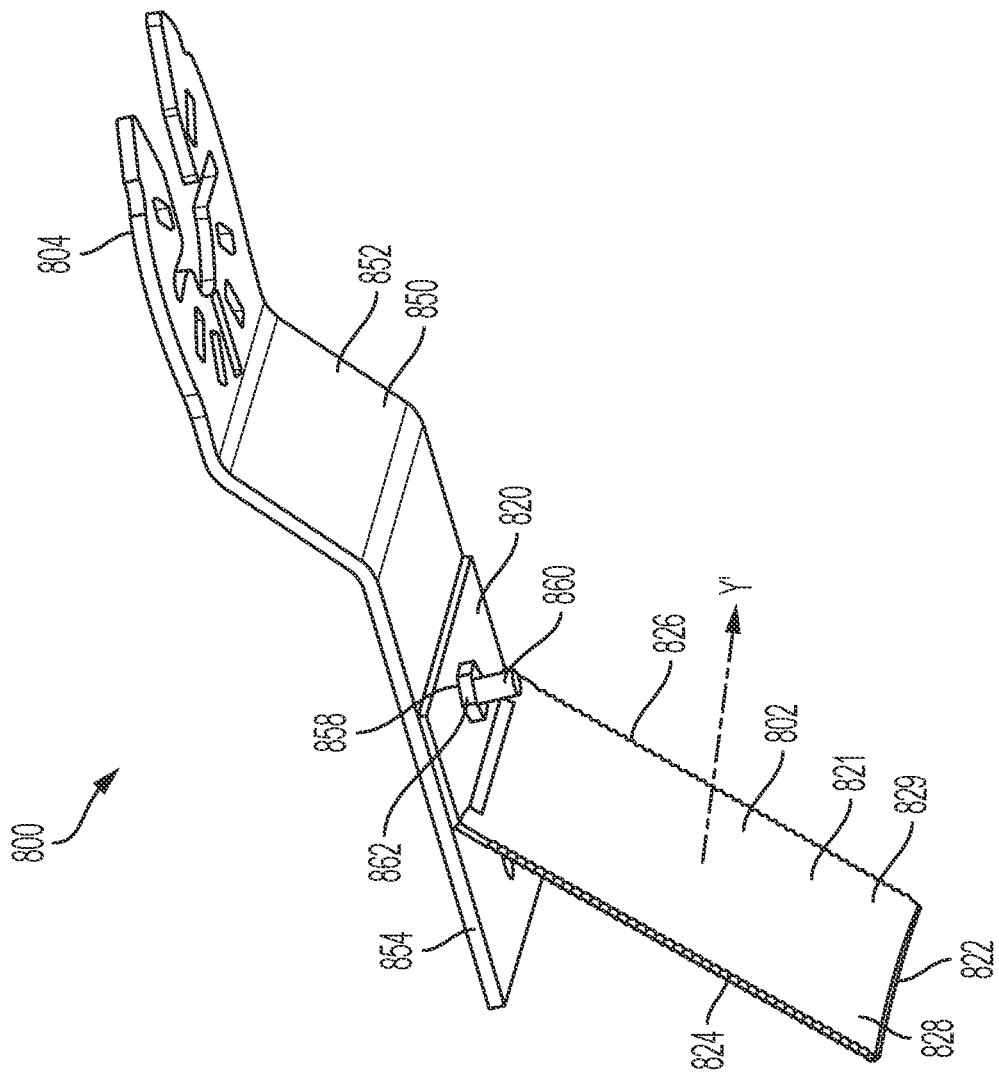
FIG. 23 is a bottom perspective view of the accessory of FIG. 22, shown in the first position.
Figure 24:
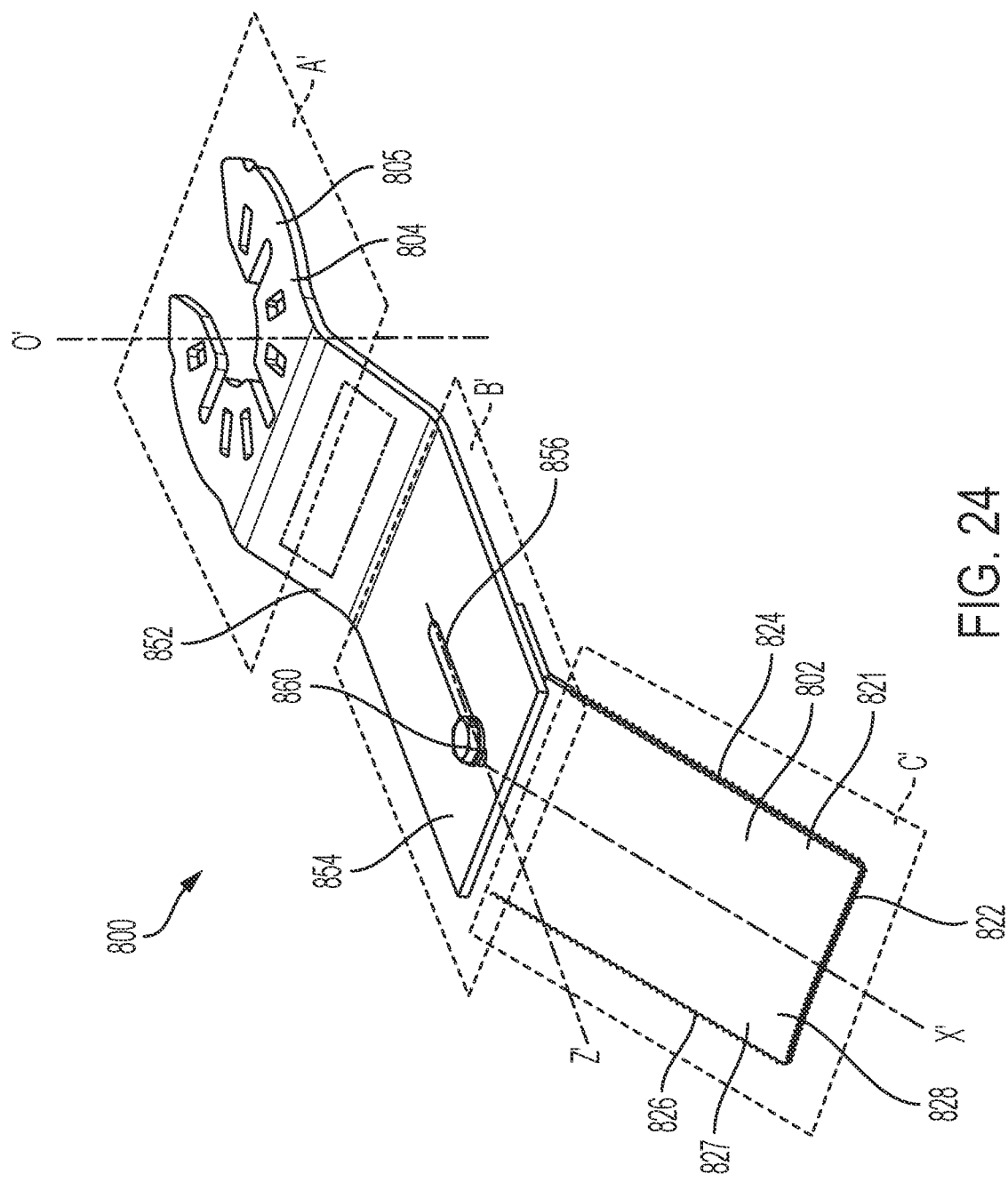
FIG. 24 is a top perspective view of the accessory of FIG. 22, shown in a second position.
Figure 25:
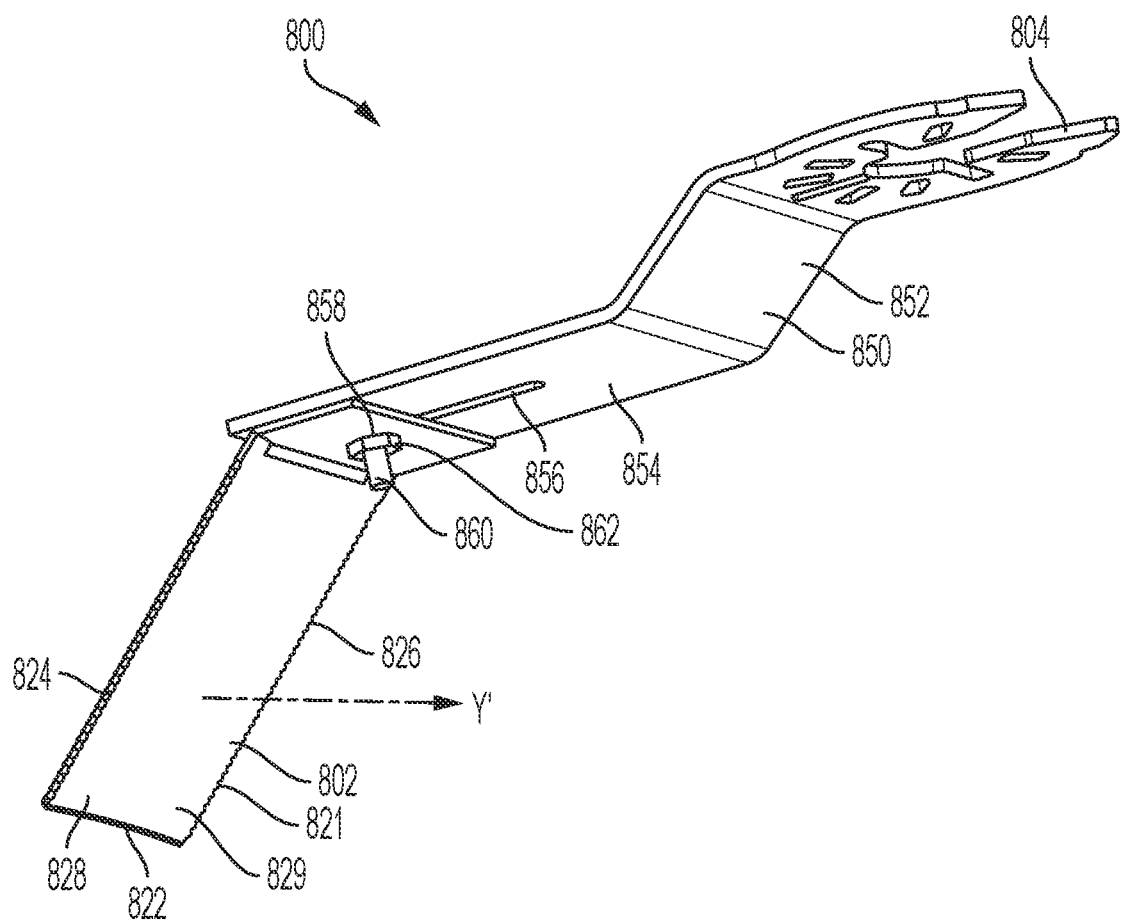
FIG. 25 is a bottom perspective view of the accessory of FIG. 22, shown in the second position.
Figure 26:
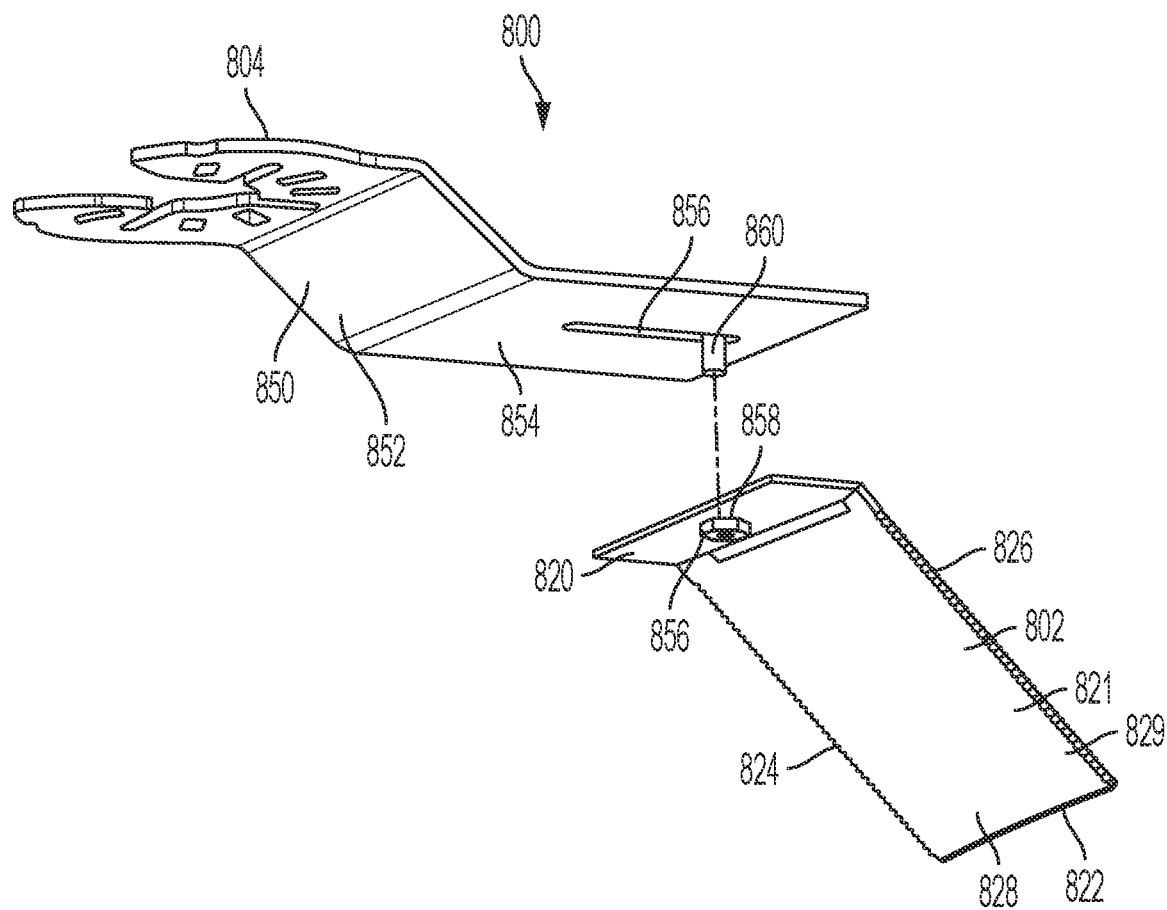
FIG. 26 is an exploded bottom perspective view of the accessory of FIG. 22.
Figure 27:
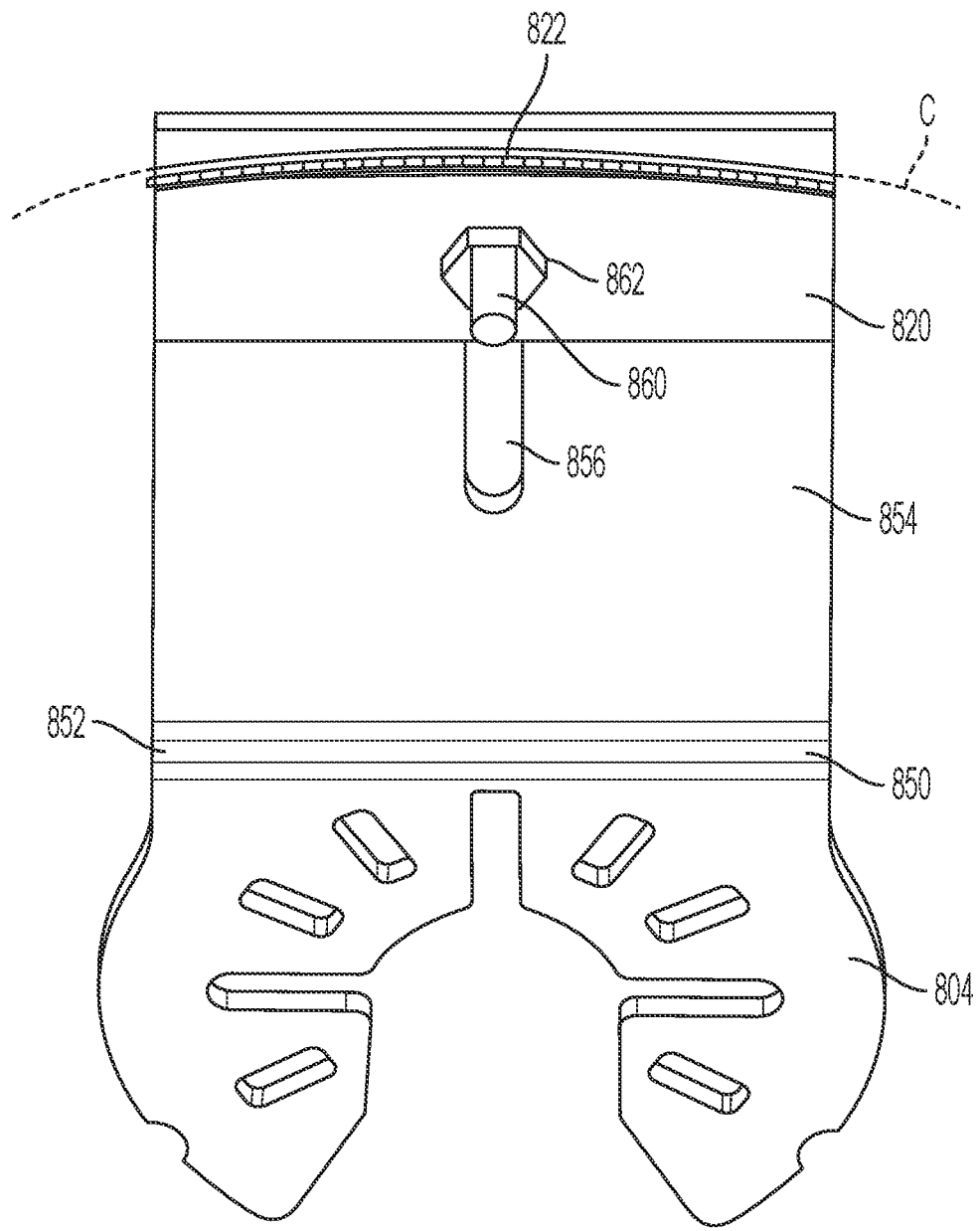
FIG. 27 is a front view of the accessory of FIG. 22.

Unlike the oscillating accessory 600, the intermediate portion 850 of the oscillating accessory 800 includes an angled surface 852 at that extends from and is transverse to the first plane A' and a horizontal surface 854 that is generally parallel to the first plane A', such that the horizontal surface is offset from the attachment portion 804. The horizontal surface 854 defines an axial slot 856 therethrough that extends along an axis Z' that is parallel to the first plane A'. The horizontal surface 854 abuts against the rear end portion 820 of the working portion 802. The rear end portion 820 defines an opening 858 therethrough. A threaded bolt 860 is received through the axial slot 856 and the opening 858 and a nut 862 may be threaded into the bolt 860 and tightened to releasably secure the working portion 802 to the intermediate portion 850. When the nut 862 is loosened, the threaded bolt 860 can be moved along the axial slot 802, causing the working portion 802 to move between a rearmost position closer to the attachment portion 804 (as shown in FIGS. 22 and 23) and a forwardmost position further from the attachment portion 804 (as shown in FIGS. 24 and 25). This enables the adjustment of the position of the working portion 802 relative to the attachment portion 804 along the axis Z' in any number of positions between the rearmost and forwardmost positions. In an implementation, the threaded bolt 860 may be integral with the working portion 802. In another implementation, the threaded bolt 860 and the opening 858 in the working portion 802 may have a non-circular (e.g., double-D shaped) cross-section to inhibit pivoting movement between the working portion 802 and the intermediate portion 850. In yet other implementations, the intermediate portion 850 may have a plurality of slots and the working portion 802 may have a plurality of openings that receive a plurality of threaded bolts therethrough. In another implementation, the axial slot may be defined in the working portion and the opening may be defined in the intermediate portion.

Example implementations have been provided so that this disclosure will be thorough, and to fully convey the scope to those who are skilled in the art. Numerous specific details are set forth such as examples of specific components, devices, and methods, to provide a thorough understanding of implementations of the present disclosure. It will be apparent to those skilled in the art that specific details need not be employed, that example implementations may be embodied in many different forms and that neither should be construed to limit the scope of the disclosure. In some example implementations, well-known processes, well-known device structures, and well-known technologies are not described in detail.

The terminology used herein is for the purpose of describing particular example implementations only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example implementations.

Terms of degree such as "generally," "substantially," "approximately," and "about" may be used herein when describing the relative positions, sizes, dimensions, or values of various elements, components, regions, layers and/or sections. These terms mean that such relative positions, sizes, dimensions, or values are within the defined range or comparison (e.g., equal or close to equal) with sufficient precision as would be understood by one of ordinary skill in the art in the context of the various elements, components, regions, layers and/or sections being described.

Numerous modifications may be made to the exemplary implementations described above. These and other implementations are within the scope of this application.

What is claimed is:

1. An oscillating accessory comprising:
an attachment portion configured to be coupled to an oscillating power tool to oscillate about an oscillating axis;
an inclined portion integrally attached to the attachment portion at an angle to the attachment portion; and
a working portion extending generally along a longitudinal axis that is transverse to the oscillating axis, the working portion having a rear end portion integrally attached to the inclined portion, a front cutting edge opposite the rear end portion, a first side edge extending from the front cutting edge to the rear end portion, and a second side edge opposite the first side edge and extending from the front cutting edge to the rear end portion, the working portion including an at least partially curved surface that contains and is curved along the longitudinal axis and along substantially an entire length of the working portion from the rear end portion to the front cutting edge, at least a portion of the first side edge including a first side cutting edge portion, wherein the working portion is configured to cut a curved opening in a workpiece.

2. The accessory of claim 1, wherein the second side edge comprises a second side cutting edge portion.

3. The accessory of claim 1, wherein the attachment portion includes a planar portion that lies generally in a first plane.

4. The accessory of claim 3, wherein the at least partially curved surface is tangent at the longitudinal axis to a second plane that is generally parallel to the first plane.

5. The accessory of claim 4, wherein the at least partially curved surface has a concave face that faces away from the attachment portion.

6. The accessory of claim 4, wherein the at least partially curved surface has a concave face that faces toward the attachment portion.

7. The accessory of claim 1, wherein the longitudinal axis is parallel to an oscillating axis about which the attachment portion oscillates when the attachment portion is coupled to the oscillating power tool.

8. The accessory of claim 1, wherein the at least partially curved surface has a radius of curvature.

9. The accessory of claim 8, wherein the radius of curvature is centered at the oscillating axis.

10. The accessory of claim 8, wherein the radius of curvature is between approximately 2 inches and approximately 8 inches.

11. The accessory of claim 1, wherein the front cutting edge has a first plurality teeth and the first side cutting edge portion has a second plurality of teeth.

12. The accessory of claim 1, wherein a position of the working portion relative to the attachment portion is user adjustable between a rear position and a forward position, the rear position being closer to the attachment portion than the forward position.

13. The accessory of claim 12, further comprising an intermediate portion coupled between the attachment portion and the working portion, wherein at least one of the intermediate portion, the working portion, and the attachment portion defines a slot therethrough to facilitate the user adjustment of the position of the working portion between the rear position and the forward position.

14. The accessory of claim 13, further comprising a fastener receivable in the slot and configured to retain the working portion in a plurality of positions between the rear position and the forward position.

15. The accessory of claim 1, further comprising an intermediate portion disposed between the attachment portion and the working portion, such that the attachment portion is offset from the working portion.

16. The accessory of claim 1, wherein the at least partially curved surface defines a cord extending from the first side edge to a second side edge.

17. The accessory of claim 16, wherein the cord has a cord length between approximately 0.70 inches and approximately 2 inches.

18. The accessory of claim 17, wherein the at least partially curved surface defines a sagitta extending from the longitudinal axis to the cord perpendicular to the cord.

19. The accessory of claim 18, wherein the sagitta has a length between approximately 0.015 inches and approximately 0.127 inches.

20. The accessory of claim 1, wherein the front cutting edge has a front curvature that matches a curvature of the at least partially curved surface of the working portion.

* * * * *